(12) United States Patent
Bell et al.

(10) Patent No.: US 9,296,750 B2
(45) Date of Patent: Mar. 29, 2016

(54) SPIROLACTAM CGRP RECEPTOR ANTAGONISTS

(71) Applicant: Merck Sharp & Dohme Corp., Rahway, NJ (US)

(72) Inventors: Ian M. Bell, Plainsboro, NJ (US); Mark Fraley, North Wales, PA (US); Tesfaye Biftu, Freehold, NJ (US); Cheng Zhu, Edison, NJ (US); Anilkumar Nair, Plainsboro, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/399,438

(22) PCT Filed: May 3, 2013

(86) PCT No.: PCT/US2013/039364
§ 371 (c)(1),
(2) Date: Nov. 6, 2014

(87) PCT Pub. No.: WO2013/169567
PCT Pub. Date: Nov. 14, 2013

(65) Prior Publication Data
US 2015/0111914 A1 Apr. 23, 2015

Related U.S. Application Data

(60) Provisional application No. 61/644,641, filed on May 9, 2012.

(51) Int. Cl.
C07D 471/10 (2006.01)
C07D 491/22 (2006.01)
C07D 471/04 (2006.01)
C07D 491/107 (2006.01)
C07D 491/20 (2006.01)

(52) U.S. Cl.
CPC ............ C07D 471/10 (2013.01); C07D 471/04 (2013.01); C07D 491/107 (2013.01); C07D 491/20 (2013.01); C07D 491/22 (2013.01)

(58) Field of Classification Search
CPC ............. C07D 471/04; C07D 491/107; C07D 491/20; C07D 471/10
USPC ............................................. 546/15; 514/278
See application file for complete search history.

(56) References Cited

U.S. PATENT DOCUMENTS 7,288,559 B2 10/2007 Bell et al.
7,390,798 B2 6/2008 Williams et al.
2010/0179166 A1 7/2010 Bell et al.

*Primary Examiner* — Rita Desai
(74) *Attorney, Agent, or Firm* — H. Eric Fischer; John C. Todaro

(57) ABSTRACT

The present invention is directed to spirolactam analogs which are antagonists of CGRP receptors and useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

3 Claims, No Drawings

SPIROLACTAM CGRP RECEPTOR ANTAGONISTS

CROSS-REFERENCE TO RELATED APPLICATIONS

This application is the national stage entry of International Patent Application Serial No. PCT/US2013/039364, filed May 3, 2013, which in turn claims the priority of U.S. provisional application Ser. No. 61/644,641 filed May 9, 2012, which applications are incorporated herein in their entirety by reference thereto.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to the CGRP receptor which is a heterodimer consisting of the G-protein coupled calcitonin-like receptor (CLR) in association with the single transmembrane protein known as receptor activity modifying protein 1 ($RAMP_1$). CGRP receptors are predominantly coupled to the activation of adenylyl cyclase and have been identified and pharmacologically evaluated in several tissues and cells, including those of brain, cardiovascular, endothelial, and smooth muscle origin.

CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al. (1990) *Ann. Neurol.* 28, 183-187), salivary levels of CGRP are elevated in migraine subjects between (Bellamy et al. (2006) *Headache* 46, 24-33) and during attacks (Cady et al. (2009) *Headache* 49, 1258-1266), and CGRP itself has been shown to trigger migrainous headache (Lassen et al. (2002) *Cephalalgia* 22, 54-61). In clinical trials, the CGRP receptor antagonist BIBN4096BS has been shown to be effective in treating acute attacks of migraine (Olesen et al. (2004) *New Engl. J. Med.* 350, 1104-1110) and was able to prevent headache induced by CGRP infusion in a control group (Petersen et al. (2005) *Clin. Pharmacol. Ther.* 77, 202-213). The orally bioavailable CGRP receptor antagonist telcagepant has also shown antimigraine effectiveness in phase III clinical trials (Ho et al. (2008) *Lancet* 372, 2115-2123; Connor et al. (2009) *Neurology* 73, 970-977).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al. (1988) *Ann. Neurol.* 23, 193-196). Electrical stimulation of the dura mater in rats increased the diameter of the middle meningeal artery, an effect that was blocked by prior administration of CGRP(8-37), a peptide CGRP receptor antagonist (Williamson et al. (1997) *Cephalalgia* 17, 525-531). Trigeminal ganglion stimulation increased facial blood flow in the rat, which was inhibited by CGRP(8-37) (Escott et al. (1995) *Brain Res.* 669, 93-99). Electrical stimulation of the trigeminal ganglion in marmoset produced an increase in facial blood flow that could be blocked by the non-peptide CGRP receptor antagonist BIBN4096BS (Doods et al. (2000) *Br. J. Pharmacol.* 129, 420-423). Thus the vascular effects of CGRP may be attenuated, prevented or reversed by a CGRP receptor antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al. (2000) *Ann. Neurol.* 47, 614-624). A CGRP antagonist may be beneficial in attenuating, preventing or reversing the effects of neuronal sensitization.

The ability of the compounds of the present invention to act as CGRP receptor antagonists makes them useful pharmacological agents for disorders that involve CGRP in humans and animals, but particularly in humans. Such disorders include migraine and cluster headache (Doods (2001) *Curr. Opin. Invest. Drugs* 2, 1261-1268; Edvinsson et al. (1994) *Cephalalgia* 14, 320-327); chronic tension type headache (Ashina et al. (2000) *Neurology* 14, 1335-1340); pain (Yu et al. (1998) *Eur. J. Pharmacol.* 347, 275-282); chronic pain (Hulsebosch et al. (2000) *Pain* 86, 163-175); neurogenic inflammation and inflammatory pain (Holzer (1988) *Neuroscience* 24, 739-768; Delay-Goyet et al. (1992) *Acta Physiol. Scanda.* 146, 537-538; Salmon et al. (2001) *Nature Neurosci.* 4, 357-358); eye pain (May et al. (2002) *Cephalalgia* 22, 195-196), tooth pain (Awawdeh et al. (2002) *Int. Endocrin. J.* 35, 30-36), non-insulin dependent diabetes mellitus (Molina et al. (1990) *Diabetes* 39, 260-265); vascular disorders; inflammation (Zhang et al. (2001) *Pain* 89, 265); arthritis, bronchial hyperreactivity, asthma, (Foster et al. (1992) *Ann. NY Acad. Sci.* 657, 397-404; Schini et al. (1994) *Am. J. Physiol.* 267, H2483-H2490; Zheng et al. (1993) *J. Virol.* 67, 5786-5791); shock, sepsis (Beer et al. (2002) *Crit. Care Med.* 30, 1794-1798); opiate withdrawal syndrome (Salmon et al. (2001) *Nature Neurosci.* 4, 357-358); morphine tolerance (Menard et al. (1996) *J. Neurosci.* 16, 2342-2351); hot flashes in men and women (Chen et al. (1993) *Lancet* 342, 49; Spetz et al. (2001) *J. Urology* 166, 1720-1723); allergic dermatitis (Wallengren (2000) *Contact Dermatitis* 43, 137-143); psoriasis; encephalitis, brain trauma, ischaemia, stroke, epilepsy, and neurodegenerative diseases (Rohrenbeck et al. (1999) *Neurobiol. Dis.* 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al. (2002) *J. Membr. Biol.* 189, 225); obesity (Walker et al. (2010) *Endocrinology* 151, 4257-4269); inflammatory bowel disease, irritable bowel syndrome, (Hoffman et al. (2002) *Scand. J. Gastroenterol.* 37, 414-422) and cystitis. Of particular importance is the acute or prophylactic treatment of headache, including migraine and cluster headache.

SUMMARY OF THE INVENTION

The present invention is directed to spirolactam analogues which are potent antagonists of CGRP receptors and may be useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of Formula I:

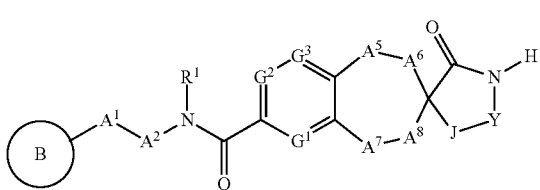

or a pharmaceutically acceptable salt thereof, wherein:
B is selected from the group consisting of $C_{3-10}$cycloalkyl, phenyl, naphthyl, tetrahydronaphthyl, indanyl, biphenyl, phenanthryl, anthryl, azepanyl, azepinyl, azetidinyl, benzimidazolyl, benzisoxazolyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuryl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isoxazolyl, isoxazolinyl, isoxazolidinyl, morpholinyl, naphthyridinyl, oxazolyl, oxazolinyl, oxazolidinyl, oxazepanyl, oxadiazolyl, 2-oxoazepinyl, 4-oxonaphthyridinyl, 2-oxopiperazinyl, 2-oxopiperidinyl, 2-oxopyrrolidinyl, 2-oxopyridinyl, 2-oxoquinolinyl, 2-oxobenzimidazolinyl, phthalazinyl, piperidinyl, piperazinyl, pyrazinyl, pyrazolidinyl, pyrazolyl, pyridazinyl, pyridyl, pyrimidinyl, pyrimidyl, pyrrolidinyl, quinazolinyl, quinolinyl, quinoxalinyl, tetrahydrofuryl, tetrahydropyranyl, tetrahydrothiopyranyl, tetrahydroimidazopyridinyl, tetrahydroisoquinolinyl, tetrahydroquinolinyl, tetrazolyl, thiamorpholinyl, thiamorpholinyl sulfoxide, thiazepinyl, thiazolyl, thiazolinyl, thiazolidinyl, thienyl, thienofuryl, thienothienyl, triazolinyl and triazolyl, wherein B is optionally substituted with 1-7 substituents each independently selected from the group consisting of:
(1) —$C_{1-6}$alkyl, which is optionally substituted with 1-7 substituents each independently selected from the group consisting of:
(a) halo,
(b) —$OR^a$,
(c) —$C_{3-6}$cycloalkyl,
(d) phenyl or heterocycle, wherein the heterocycle is selected from pyridinyl, pyrimidinyl, pyrazinyl, pyridazinyl, piperidinyl, piperazinyl, pyrrolidinyl, thienyl and morpholinyl, and wherein said phenyl or heterocycle is optionally substituted with 1-5 substituents each independently selected from the group consisting of:
(i) —$C_{1-6}$alkyl,
(ii) —O—$C_{1-6}$alkyl,
(iii) halo,
(iv) hydroxy,
(v) trifluoromethyl, and
(vi) —$OCF_3$,
(e) —$CO_2R^a$,
(f) —$NR^bR^c$,
(g) —$SO_2R^d$,
(h) —$CONR^bR^c$,
(i) trifluoromethyl,
(j) —$OCO_2R^a$,
(k) —$(NR^b)CO_2R^a$,
(l) —$O(CO)NR^bR^c$, and
(m) —$(NR^a)(CO)NR^bR^c$,
(2) —$C_{3-6}$cycloalkyl, which is optionally substituted with 1-7 substituents each independently selected from the group consisting of:
(a) halo,
(b) —$OR^a$,
(c) trifluoromethyl, and
(d) phenyl, which is optionally substituted with 1-5 substituents each independently selected from the group consisting of:
(i) —$C_{1-6}$alkyl,
(ii) —O—$C_{1-6}$alkyl,
(iii) halo,
(iv) hydroxyl, and
(v) trifluoromethyl,
(3) phenyl or heterocycle, wherein the heterocycle is selected from pyridinyl, pyrimidinyl, pyrazinyl, thienyl, pyridazinyl, pyrrolidinyl, azetidinyl, thiazolyl, isothiazolyl, oxazolyl, isoxazolyl, imidazolyl, triazolyl, tetrazolyl, azepanyl, benzimidazolyl, benzopyranyl, benzofuryl, benzothiazolyl, benzoxazolyl, chromanyl, furyl, imidazolidinyl, imidazolinyl, indazolyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, quinazolinyl, 1,3-dioxolanyl, oxadiazolyl, piperidinyl and morpholinyl, and wherein the phenyl or heterocycle is optionally substituted with 1-5 substituents each independently selected from the group consisting of:
(a) —$C_{1-6}$alkyl which is optionally substituted with 1-6 fluoro,
(b) halo,
(c) —$OR^a$,
(d) —$C_{3-6}$cycloalkyl,
(e) phenyl or heterocycle, wherein the heterocycle is selected from pyridinyl, pyrimidinyl, pyrazinyl, thienyl and morpholinyl,
and wherein the phenyl or heterocycle is optionally substituted with 1-5 substituents each independently selected from the group consisting of:
(i) —$C_{1-6}$alkyl,
(ii) —O—$C_{1-6}$alkyl,
(iii) halo,
(iv) hydroxy and
(v) trifluoromethyl,
(f) —$CO_2R^a$,
(g) —$NR^bR^c$,
(h) —$CONR^bR^c$, (i) —SO$_2$R$^d$, and
(j) oxo,
(4) halo,
(5) oxo,
(6) —OR$^a$,
(7) —CN,
(8) —CO$_2$R$^a$,
(9) —NR$^b$R$^c$,
(10) —SO$_2$R$^d$,
(11) —CONR$^b$R$^c$,
(12) —OCO$_2$R$^a$,
(13) —(NR$^b$)CO$_2$R$^a$,
(14) —(NR$^b$)(CO)NR$^b$R$^c$,
(15) —SO$_2$NR$^b$R$^c$, and
(16) —S(O)$_v$R$^d$;

or wherein two of the substituents on B and the atom(s) to which they are attached are joined to form a ring selected from azetidinyl, azepanyl, azepinyl, cyclopropyl, cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, thiadiazolyl, oxadiazolyl, isoxazolyl, pyrazolyl, triazolyl, pyridinyl, pyrimidinyl, pyrazinyl, pyridazinyl, triazinyl, pyrrolyl, pyrrolinyl, morpholinyl, azetidinyl, pyrrolidinyl, piperidinyl, tetrahydrofuranyl, tetrahydropyranyl, tetrahydropyridinyl, furanyl, dihydrofuranyl, dihydropyranyl, dihydrothienyl, tetrahydrothienyl, dihydrothiopyranyl, tetrahydrothiopyranyl, pyrrolidinyl, piperidinyl, and piperazinyl, which ring is optionally substituted with 1-5 substituents each independently selected from the group consisting of:

(a) —C$_{1-6}$alkyl, which is optionally substituted with 1-3 substituents each independently selected from the group consisting of:
  (i) halo,
  (ii) —OR$^a$,
  (iii) —C$_{3-6}$cycloalkyl, which is optionally substituted with 1-5 substituents each independently selected from the group consisting of:
    (I) —C$_{1-6}$alkyl,
    (II) —O—C$_{1-6}$alkyl,
    (III) halo, and
    (IV) hydroxy,
  (iv) phenyl or heterocycle, wherein the heterocycle is selected from pyridinyl, pyrimidinyl, pyrazinyl, pyridazinyl, piperidinyl, piperazinyl, pyrrolidinyl, thienyl and morpholinyl, which phenyl or heterocycle is optionally substituted with 1-5 substituents each independently selected from the group consisting of:
    (I) —C$_{1-6}$alkyl,
    (II) —O—C$_{1-6}$alkyl,
    (III) halo,
    (IV) hydroxy,
    (V) trifluoromethyl, and
    (VI) —OCF$_3$,
  (v) —CO$_2$R$^a$,
  (vi) —NR$^b$R$^c$, and
  (vii) —SO$_2$R$^d$,
(b) —C$_{3-6}$cycloalkyl, which is optionally substituted with 1-5 substituents each independently selected from the group consisting of:
  (i) halo,
  (ii) hydroxy,
  (iii) —O—C$_{1-6}$alkyl,
  (iv) trifluoromethyl, and
  (v) phenyl,
(c) phenyl or heterocycle, wherein the heterocycle is selected from pyridinyl, pyrimidinyl, pyrazinyl, thienyl, pyridazinyl, pyrrolidinyl, azetidinyl, piperidinyl and morpholinyl, which phenyl or heterocycle is optionally substituted with 1-3 substituents each independently selected from the group consisting of:
  (i) halo,
  (ii) hydroxy,
  (iii) —C$_{3-6}$cycloalkyl,
  (iv) —O—C$_{1-6}$alkyl which is optionally substituted with 1-6 fluoro, and
  (v) —C$_{1-6}$alkyl which is optionally substituted with 1-6 fluoro,
(d) halo,
(e) —SO$_2$R$^d$,
(f) —OR$^a$,
(g) oxo,
(h) —CN,
(i) —COR$^a$,
(j) —NR$^b$R$^c$,
(k) —CONR$^b$R$^c$, and
(l) —CO$_2$R$^a$;

A$^1$ is selected from:
(1) a bond,
(2) —CR$^8$R$^9$—,
(3) —CH$_2$CR$^8$R$^9$—, or
(4) —C(=O)—;

A$^2$ is selected from:
(1) a bond,
(2) —CR$^8$R$^9$—,
(3) —CH$_2$CR$^8$R$^9$—, or
(4) —C(=O)—;

A$^5$ is selected from:
(1) —O—,
(2) —S(O)$_v$—,
(3) —CR$^{6a}$R$^{6b}$—,
(4) —CR$^{6a}$H,
(5) —CH$_2$—,
(6) —N(R$^7$)—,
(7) —(C=O)—, or
(8) a bond, A$^6$ is selected from:
(1) —O—,
(2) —S(O)$_v$—,
(3) —CR$^{6a}$R$^{6b}$—,
(4) —CR$^{6a}$H,
(5) —CH$_2$—,
(6) —N(R$^7$)—, or
(7) —(C=O)—, A$^7$ is selected from:
(1) —O—,
(2) —S(O)$_v$—,
(3) —CR$^{6a}$R$^{6b}$—,
(4) —CR$^{6a}$H,
(5) —CH$_2$—,
(6) —N(R$^7$)—,
(7) —(C=O)—, or
(8) a bond, A$^8$ is selected from:
(1) —O—,
(2) —S(O)$_v$—,
(3) —CR$^{6a}$R$^{6b}$—,
(4) —CR$^{6a}$H,
(5) —CH$_2$—,
(6) —N(R$^7$)—, or
(7) —(C=O)—, wherein at least one of A$^5$, A$^6$, A$^7$, and A$^8$ is selected from:
(a) —CR$^{6a}$R$^{6b}$—,
(b) —CR$^{6a}$H—, (c) —O—,
(d) —S(O)$_v$—,
(e) —N(R$^7$)—, or
(f) —(C=O)—, G$^1$ is selected from:
(1) —C(R$^{2a}$)=,
(2) —N=, or
(3) —(N$^+$—O$^-$)=;

G$^2$ is selected from:
(1) —C(R$^{2b}$)=,
(2) —N=, or
(3) —(N$^+$—O$^-$)=;

G$^3$ is selected from:
(1) —C(R$^{2c}$)=,
(2) —N=, or
(3) —(N$^+$—O$^-$)=;

R$^1$ is selected from:
(1) hydrogen,
(2) C$_{1-6}$ alkyl which is optionally substituted with 1-6 fluoro,
(3) C$_{5-6}$ cycloalkyl,
(4) benzyl or
(5) phenyl, or R$^1$ is joined to B to form a ring selected from piperidinyl, pyrrolidinyl, piperazinyl, azetidinyl, azepinyl and morpholinyl, which ring is optionally substituted with 1-5 substituents each independently selected from the group consisting of:
(1) —C$_{1-6}$alkyl,
(2) —O—C$_{1-6}$alkyl,
(3) halo,
(4) hydroxy,
(5) phenyl, and
(6) benzyl;

R$^{2a}$, R$^{2b}$ and R$^{2c}$ are each independently selected from the group consisting of:
(1) hydrogen,
(2) —C$_{1-6}$alkyl, which is optionally substituted with 1-6 halo,
(3) halo,
(4) —OR$^a$, and
(5) —CN;

J is selected from:
(1) =C(R$^{3a}$)—,
(2) —CR$^4$R$^5$—,
(3) —C(=O)—, or
(4) —N(R$^b$)—;

Y is selected from:
(1) =C(R$^{3b}$)—,
(2) —CR$^4$R$^5$—,
(3) —C(=O)—,
(4) =N—, or
(5) —N(R$^b$)—;

R$^{3a}$ and R$^{3b}$ are each independently selected from the group consisting of:
(1) hydrogen,
(2) —C$_{1-4}$alkyl, which is optionally substituted with 1-5 substituents each independently selected from the group consisting of:
(a) halo,
(b) —OR$^a$,
(c) —C$_{3-6}$cycloalkyl, and
(d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is optionally substituted with 1-3 substituents each independently selected from the group consisting of:
(i) halo,
(ii) —OR$^a$,
(iii) —CN, and
(iv) C$_{1-6}$alkyl, which is optionally substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is optionally substituted with 1-3 substituents each independently selected from the group consisting of:
(a) halo,
(b) —OR$^a$,
(c) —C$_{3-6}$cycloalkyl,
(d) —C$_{1-4}$alkyl which is optionally substituted with 1-6 halo, and
(e) phenyl, which is optionally substituted with 1-5 substituents each independently selected from the group consisting of:
(i) halo,
(ii) —C$_{1-6}$alkyl, which is optionally substituted with 1-6 halo, and
(iii) —OR$^a$,
(4) halo,
(5) —OR$^a$,
(6) —CN,
(7) —CO$_2$R$^a$,
(8) —NR$^b$R$^c$, and
(9) —C(=O)NR$^b$R$^c$;

or R$^{3a}$ and R$^{3b}$ and the carbon atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is optionally substituted with 1-5 substituents each independently selected from the group consisting of:
(a) —C$_{1-6}$alkyl, which is optionally substituted with 1-3 substituents each independently selected from the group consisting of:
(i) halo,
(ii) —OR$^a$,
(iii) —C$_{3-6}$cycloalkyl, and
(iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is optionally substituted with 1-5 substituents each independently selected from the group consisting of:
(I) —OR$^a$,
(II) halo,
(III) —CN, and
(IV) —C$_{1-6}$alkyl which is optionally substituted with 1-6 halo,
(v) —CO$_2$R$^a$,
(vi) —NR$^b$R$^c$,
(vii) —S(O)$_v$R$^d$,
(viii) —C(=O)NR$^b$R$^c$,
(ix) —N(R$^b$)CO$_2$R$^a$, and
(x) —N(R$^b$)SO$_2$R$^d$, (b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is optionally substituted with 1-5 substituents each independently selected from the group consisting of:
  (i) halo,
  (ii) —OR$^a$,
  (iii) —CN, and
  (iv) —C$_{1-6}$alkyl which is optionally substituted with 1-6 halo,
(c) halo,
(d) —S(O)$_v$R$^d$,
(e) —OR$^a$,
(f) —CN,
(g) —C(=O)R$^a$,
(h) —NR$^b$R$^c$,
(i) —C(=O)NR$^b$R$^c$,
(j) —CO$_2$R$^a$,
(k) —(NR$^b$)CO$_2$R$^a$,
(l) —O—(C=O)—NR$^b$R$^c$,
(m) —(NR$^b$)—(C=O)—NR$^b$R$^c$,
(n) oxido,
(o) oxo, and
(p) —(NR$^b$)SO$_2$R$^d$;

R$^4$ and R$^5$ are each independently selected from the group consisting of:
(1) hydrogen,
(2) halo,
(3) —OR$^a$,
(4) —C$_{1-6}$alkyl, which is optionally substituted with 1-4 substituents each independently selected from the group consisting of:
  (a) halo,
  (b) —OR$^a$,
  (c) —CN, and
  (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is optionally substituted with 1-5 substituents each independently selected from the group consisting of:
    (i) —OR$^a$,
    (ii) halo,
    (iii) —CN and
    (iv) —C$_{1-6}$alkyl which is optionally substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is optionally substituted with 1-5 substituents each independently selected from the group consisting of:
  (a) halo,
  (b) —CN,
  (c) —OR$^a$,
  (d) nitro, and
  (e) —C$_{1-6}$alkyl which is optionally substituted with 1-6 halo;
or R$^4$ and R$^5$ and the atom to which they are attached join to form a 4-, 5-, or 6-membered ring optionally containing a heteroatom selected from N, O, and S, wherein the sulfur is optionally oxidized to the sulfone or sulfoxide, which ring is optionally substituted with 1-4 substituents each independently selected from the group consisting of:
  (a) halo,
  (b) —OR$^a$,
  (c) —C$_{1-6}$alkyl, which is optionally substituted with 1-6 halo, and
  (d) phenyl;

R$^{6a}$ and R$^{6b}$ are each independently selected from the group consisting of:
(1) —C$_{1-6}$alkyl, which is optionally substituted with 1-5 substituents each independently selected from the group consisting of:
  (a) halo,
  (b) —OR$^a$,
  (c) —C$_{3-6}$cycloalkyl,
  (d) phenyl or heterocycle, wherein said heterocycle is selected from: pyridyl, pyrimidinyl, pyrazinyl, pyridazinyl, piperdinyl, piperazinyl, pyrrolidinyl, thienyl, morpholinyl, thiazolyl and oxazolyl, which phenyl or heterocycle is optionally substituted with 1-5 substituents each independently selected from the group consisting of:
    (i) halo,
    (ii) —C$_{1-6}$alkyl, which is optionally substituted with 1-5 halo, and
    (iii) —OR$^a$,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —CF$_3$,
  (m) —O—CO$_2$R$^d$,
  (n) —O—(C=O)—NR$^b$R$^c$,
  (o) —NR$^b$—(C=O)—NR$^b$R$^c$, and
  (p) —C(=O)R$^a$,
(2) —C$_{1-6}$cycloalkyl, which is optionally substituted with 1-5 substituents each independently selected from the group consisting of:
  (a) halo,
  (b) —CN,
  (c) —C$_{1-6}$alkyl, which is optionally substituted with 1-5 halo,
  (d) —OR$^a$, and
  (e) phenyl, which is optionally substituted with 1-5 substituents where the substituents are each independently selected from the group consisting of:
    (i) —OR$^a$,
    (ii) halo,
    (iii) —CN, and
    (iv) —C$_{1-6}$alkyl, which is optionally substituted with 1-5 halo,
(3) phenyl or heterocycle, wherein said heterocycle is selected from: pyridyl, pyrimidinyl, pyrazinyl, pyridazinyl, piperdinyl, piperazinyl, pyrrolidinyl, thienyl, morpholinyl, thiazolyl and oxazolyl, which phenyl or heterocycle is optionally substituted with 1-5 substituents each independently selected from the group consisting of:
  (a) halo,
  (b) —OR$^a$,
  (c) —C$_{3-6}$cycloalkyl, (d) phenyl, which is optionally substituted with 1-5 substituents each independently selected from the group consisting of:
(i) halo,
(ii) —$C_{1-6}$alkyl, which is optionally substituted with 1-6 halo, and
(iii) —OR$^a$,
(e) —$CO_2R^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$,
(o) —C(=O)R$^a$, and
(p) —$C_{1-6}$alkyl, which is optionally substituted with 1-6 halo,
(4) halo,
(5) oxo,
(6) —OR$^a$,
(7) —CN,
(8) —CO$_2$R$^a$,
(9) —C(=O)R$^a$,
(10) —NR$^b$R$^c$,
(11) —S(O)$_v$R$^d$,
(12) —C(=O)NR$^b$R$^c$,
(13) —O—CO$_2$R$^d$,
(14) —N(R$^b$)CO$_2$R$^d$,
(15) —O—(C=O)—NR$^b$R$^c$,
(16) —NR$^b$—(C=O)—NR$^b$R$^c$,
(17) —SO$_2$NR$^b$R$^c$,
(18) —N(R$^b$)SO$_2$R$^d$,
or R$^{6a}$ and R$^{6b}$ and the carbon atom(s) to which they are attached join to form a ring selected from cyclopropyl, cyclobutyl, cyclopentyl, cyclohexyl, cycloheptyl, aziridinyl, azetidinyl, pyrrolidinyl, piperidinyl, piperazinyl, morpholinyl, thietanyl and tetrahydrothienyl, wherein the sulfur is optionally oxidized to the sulfone or sulfoxide, which ring is optionally substituted with 1-5 substituents each independently selected from the group consisting of:
(a) —$C_{1-6}$alkyl, which is optionally substituted with 1-3 substituents each independently selected from the group consisting of:
(i) halo,
(ii) —OR$^a$,
(iii) —$C_{3-6}$cycloalkyl,
(iv) —CO$_2$R$^a$,
(v) —NR$^b$R$^c$,
(vi) —S(O)$_v$R$^d$,
(vii) —C(=O)NR$^b$R$^c$, and
(viii) phenyl,
(b) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is optionally substituted with 1-5 substituents each independently selected from the group consisting of:
(i) halo,
(ii) —$C_{1-6}$alkyl, which is optionally substituted with 1-5 halo, and
(iii) —OR$^a$,
(c) —OR$^a$,
(d) halo,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$, and
(o) —C(=O)R$^a$;
R$^7$ is independently selected from:
(1) hydrogen,
(2) —C(=O)R$^a$,
(3) —CO$_2$R$^a$,
(4) —S(=O)R$^d$,
(5) —SO$_2$R$^d$,
(6) —C(=O)NR$^b$R$^c$,
(7) —$C_{1-6}$alkyl, which is optionally substituted with 1-5 substituents each independently selected from the group consisting of:
(a) halo,
(b) —OR$^a$,
(c) —$C_{3-6}$cycloalkyl,
(d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is optionally substituted with 1-5 substituents each independently selected from the group consisting of:
(i) halo,
(ii) —$C_{1-6}$alkyl, which is optionally substituted with 1-5 halo,
(iii) —OR$^a$,
(iv) —NR$^b$R$^c$,
(v) —C(=O)R$^a$,
(vi) —CO$_2$R$^a$, and
(vii) oxo,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —CF$_3$,
(m) —O—CO$_2$R$^d$,
(n) —O—(C=O)—NR$^b$R$^c$,
(o) —NR$^b$—(C=O)—NR$^b$R$^c$, and
(p) —C(=O)R$^a$,
(8) —$C_{3-6}$cycloalkyl, which is optionally substituted with 1-6 substituents each independently selected from the group consisting of:
(a) halo,
(b) —CN,
(c) —OR$^a$, and
(d) $C_{1-6}$alkyl, which is optionally substituted with 1-6 halo;
R$^8$ and R$^9$ are each independently selected from the group consisting of:
(1) hydrogen,
(2) $C_{1-6}$ alkyl, which is optionally substituted with 1-5 substituents each independently selected from the group consisting of:

(a) halo,
(b) hydroxy,
(c) —NR$^{10}$R$^{11}$,
(d) —CONR$^{10}$R$^{111}$, and
(e) —CO$_2$R$^a$,
(3) phenyl, which is optionally substituted with 1-3 substituents each independently selected from the group consisting of:
(a) C$_{1-4}$alkyl,
(b) hydroxyl and
(c) halo,
(4) —CONR$^{10}$—(C$_{1-6}$alkyl)—NR$^{12}$R$^{13}$,
(5) —CO$_2$R$^a$,
(6) —CONR$^{10}$R$^{11}$, and
(7) hydroxy,
R$^{10}$ and R$^{11}$ are each independently selected from the group consisting of:
(1) hydrogen and
(2) C$_{1-6}$ alkyl, which is optionally substituted with 1-5 substituents each independently selected from the group consisting of halo and hydroxy,
R$^{12}$ and R$^{13}$ are each independently selected from the group consisting of:
(1) hydrogen,
(2) —C$_{1-6}$alkyl,
(3) —COR$^a$, and
(4) —CO$_2$R$^a$,
R$^a$ is selected from:
(1) hydrogen,
(2) C$_{1-6}$alkyl, which is optionally substituted with 1-7 substituents each independently selected from the group consisting of:
(a) halo,
(b) —O—C$_{1-6}$alkyl, which is optionally substituted with 1-6 halo,
(c) hydroxyl,
(d) —CN, and
(e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
(i) halo,
(ii) —O—C$_{1-6}$alkyl, which is optionally substituted with 1-6 halo,
(iii) —CN,
(iv) nitro,
(v) hydroxyl, and
(vi) —C$_{1-6}$alkyl, which is optionally substituted with 1-6 halo,
(3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
(a) halo,
(b) —CN,
(c) —O—C$_{1-6}$alkyl, which is optionally substituted with 1-6 halo,
(d) nitro,
(e) hydroxyl, and
(f) —C$_{1-6}$alkyl, which is optionally substituted with 1-6 halo, and
(4) —C$_{3-6}$cycloalkyl, which is optionally substituted with 1-6 halo;
R$^b$ and R$^c$ are each independently selected from the group consisting of:
(1) hydrogen,
(2) C$_{1-6}$alkyl, which is optionally substituted with 1-7 substituents each independently selected from the group consisting of:
(a) halo,
(b) —OR$^a$,
(c) —CN,
(d) —CO$_2$R$^a$,
(e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
(i) halo,
(ii) —OR$^a$,
(iii) —C$_{1-6}$alkyl, which is optionally substituted with 1-6 halo, and
(iv) nitro,
(3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
(a) halo,
(b) —OR$^a$,
(c) —C$_{1-6}$alkyl, which is optionally substituted with 1-6 halo,
(d) —C$_{3-6}$cycloalkyl, which is optionally substituted with 1-6 halo,
(e) —CN, and
(f) —CO$_2$R$^a$, and
(4) —C$_{3-6}$cycloalkyl, which is optionally substituted with 1-6 halo;
or R$^b$ and R$^c$ and the nitrogen atom to which they are attached join to form a 4-, 5-, or 6-membered ring optionally containing an additional heteroatom selected from N, O, and S, wherein the sulfur is optionally oxidized to the sulfone or sulfoxide, which ring is optionally substituted with 1-4 substituents each independently selected from the group consisting of:
(a) halo,
(b) —OR$^a$,
(c) —C$_{1-6}$alkyl, which is optionally substituted with 1-6 halo, and
(d) phenyl;
R$^d$ is selected from the group consisting of:
(1) C$_{1-6}$alkyl, which is optionally substituted with 1-4 substituents each independently selected from the group consisting of:
(a) halo,
(b) —OR$^a$,
(c) —CO$_2$R$^a$,
(d) —CN, and
(e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
(i) halo,
(ii) —OR$^a$,
(iii) —C$_{1-6}$alkyl, which is optionally substituted with 1-6 halo, and
(iv) nitro,
(2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is optionally substituted with 1-3 substituents each independently selected from the group consisting of:
(a) halo,
(b) —OR$^a$,
(c) —C$_{1-6}$alkyl, which is optionally substituted with 1-6 halo,
(d) —C$_{3-6}$cycloalkyl, which is optionally substituted with 1-6 halo
(e) —CN, and
(f) —CO$_2$R$^a$, and
(3) —C$_{3-6}$cycloalkyl, which is optionally substituted with 1-6 halo;
v is 0, 1, or 2.

In a class of the invention, R$^1$ is hydrogen.
In a class of the invention, R$^{2a}$ is hydrogen.
In a class of the invention, R$^{2b}$ is hydrogen.
In a class of the invention, R$^{2c}$ is hydrogen.
In a class of the invention R$^{3a}$ and R$^{3b}$ are each independently selected from the group consisting of:
(1) hydrogen,
(2) —C$_{1-4}$alkyl, which is optionally substituted with 1-5 substituents each independently selected from the group consisting of:
(a) halo,
(b) —OR$^a$,
(c) —C$_{3-6}$cycloalkyl,
(d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is optionally substituted with 1-3 substituents each independently selected from the group consisting of:
(i) halo,
(ii) —OR$^a$,
(iii) —CN, and
(iv) C$_{1-6}$alkyl, which is optionally substituted with 1-6 halo,
(3) halo,
(4) —OR$^a$ and
(5) —CN,
or R$^{3a}$ and R$^{3b}$ and the carbon atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is optionally substituted with 1-5 substituents each independently selected from the group consisting of:
(a) —C$_{1-6}$alkyl, which is optionally substituted with 1-3 substituents each independently selected from the group consisting of:
(i) halo,
(ii) —OR$^a$,
(iii) —CO$_2$R$^a$,
(iv) —NR$^b$R$^c$,
(v) —S(O)$_v$R$^d$,
(vi) —C(=O)NR$^b$R$^c$,
(vii) —N(R$^b$)CO$_2$R$^a$, and
(viii) —N(R$^b$)SO$_2$R$^d$,
(b) halo,
(c) —S(O)$_v$R$^d$,
(d) —OR$^a$,
(e) —CN,
(f) —C(=O)R$^a$,
(g) —NR$^b$R$^c$,
(h) —C(=O)NR$^b$R$^c$,
(i) —CO$_2$R$^a$,
(j) —(NR$^b$)COO$_2$R$^a$,
(k) —O—(C=O)—NR$^b$R$^c$,
(l) —(NR$^b$)—(C=O)—NR$^b$R$^c$,
(m) oxido,
(n) oxo, and
(o) —(NR$^b$)SO$_2$R$^d$.

In a subclass of the invention, and R$^{3a}$ and R$^{3b}$ and the atom(s) to which they are attached join to form a ring selected from phenyl, pyridyl, and pyrimidinyl, which ring is optionally substituted with 1-3 substituents each independently selected from the group consisting of —C$_{1-6}$alkyl (which is optionally substituted with 1-3 substituents each independently selected from the group consisting of halo, —OR$^a$ and —NR$^b$R$^c$), halo, —OR$^a$, —CN, —NR$^b$R$^c$ and oxido. In a further subclass of the invention, R$^{3a}$ and R$^{3b}$ and the atom(s) to which they are attached join to form a ring selected from pyridyl, and pyrimidinyl, which ring is optionally substituted with 1-3 substituents each independently selected from the group consisting of —C$_{1-4}$alkyl (which is optionally substituted with 1-3 substituents each independently selected from the group consisting of halo, —OR$^a$ and —NR$^b$R$^c$), halo, and —CN. In a further subclass of the invention, and R$^{3a}$ and R$^{3b}$ and the atom(s) to which they are attached join to form a ring selected from pyridyl.

In a class of the invention, R$^4$ is selected from the group consisting of: hydrogen, halo, —OR$^a$ and —C$_{1-6}$alkyl (which is optionally substituted with 1-4 substituents each independently selected from the group consisting of halo and —OR$^a$). In a subclass of the invention, R$^4$ is hydrogen.

In a class of the invention, R$^5$ is selected from the group consisting of: hydrogen, halo, —OR$^a$ and —C$_{1-6}$alkyl (which is optionally substituted with 1-4 substituents each independently selected from the group consisting of halo and —OR$^a$). In a subclass of the invention, R$^5$ is hydrogen.

In a class of the invention, R$^{6a}$ and R$^{6b}$ are each independently selected from the group consisting of: —C$_{1-6}$alkyl (which is optionally substituted with 1-5 substituents each independently selected from the group consisting of halo and —OR$^a$) and halo. In a subclass of the invention, R$^{6a}$ is halo. In a subclass of the invention, R$^{6a}$ is methyl. In a subclass of the invention, R$^{6b}$ is halo.

In a class of the invention, R$^7$ is hydrogen.

In a class of the invention, R$^8$ is selected from the group consisting of hydrogen and C$_{1-6}$alkyl (which is optionally substituted with 1-5 substituents each independently selected from the group consisting of halo and hydroxy). In a subclass of the invention, R$^8$ is hydrogen.

In a class of the invention, R$^9$ is selected from the group consisting of hydrogen and C$_{1-6}$alkyl (which is optionally substituted with 1-5 substituents each independently selected from the group consisting of halo and hydroxy). In a subclass of the invention, R$^9$ is hydrogen.

In a class of the invention, $R^{10}$ is hydrogen.
In a class of the invention, $R^{11}$ is hydrogen.
In a class of the invention, $R^{12}$ is hydrogen.
In a class of the invention, $R^{13}$ is hydrogen.

In a class of the invention, $R^a$ is selected from hydrogen or $C_{1-6}$alkyl, which is optionally substituted with 1-7 substituents each independently selected from the group consisting of halo, —O—$C_{1-6}$alkyl (which is optionally substituted with 1-6 halo), hydroxyl and —CN. In a subclass of the invention, $R^a$ is hydrogen.

In a class of the invention, $R^b$ and $R^c$ are independently selected from the group consisting of hydrogen and $C_{1-6}$alkyl, which is optionally substituted with 1-7 substituents each independently selected from the group consisting of halo, —$OR^a$ and —CN. In a subclass of the invention, $R^b$ is hydrogen. In a subclass of the invention, $R^c$ is hydrogen.

In a class of the invention, $R^d$ is $C_{1-6}$alkyl, which is optionally substituted with 1-4 halo.

In a class of the invention, B is selected from the group consisting of $C_{3-10}$cycloalkyl, phenyl, azepanyl, azepinyl, azetidinyl, imidazolidinyl, imidazolinyl, imidazolyl, 2-oxoazepinyl, 2-oxopiperidinyl, 2-oxopyrrolidinyl, piperidinyl, piperazinyl, pyrazinyl, pyrazolidinyl, pyrazolyl, pyridazinyl, pyridyl, pyrimidinyl, pyrimidyl, pyrrolidinyl and tetrazolyl,
wherein B is optionally substituted with 1-7 substituents each independently selected from the group consisting of:
(1) —$C_{1-6}$alkyl, which is optionally substituted with 1-7 substituents each independently selected from the group consisting of:
 (a) halo,
 (b) —$OR^a$,
 (c) —$C_{3-6}$cycloalkyl, and
 (d) phenyl or heterocycle, wherein the heterocycle is selected from pyridinyl, pyrimidinyl, pyrazinyl, pyridazinyl, piperidinyl, piperazinyl, pyrrolidinyl, thienyl and morpholinyl, and wherein said phenyl or heterocycle is optionally substituted with 1-5 substituents each independently selected from the group consisting of —$C_{1-6}$alkyl, —O—$C_{1-6}$alkyl, halo, hydroxy, trifluoromethyl, and —OCF3,
(2) phenyl or heterocycle, wherein the heterocycle is selected from pyridinyl, pyrimidinyl, pyrazinyl, thienyl, pyridazinyl, pyrrolidinyl, azetidinyl, thiazolyl, oxazolyl, imidazolyl, indazolyl, triazolyl, tetrazolyl, azepanyl, imidazolidinyl, imidazolinyl, 2-oxopiperazinyl, 2-oxopiperidinyl, 2-oxopyrrolidinyl, pyrazolidinyl, pyrazolyl, pyrrolyl, tetrahydrofuryl, 1,3-dioxolanyl, oxadiazolyl, piperidinyl and morpholinyl, and wherein the phenyl or heterocycle is optionally substituted with 1-5 substituents each independently selected from the group consisting of:
 (a) —$C_{1-6}$alkyl which is optionally substituted with 1-6 fluoro,
 (b) halo,
 (c) hydroxy, and
 (d) —O—$C_{1-6}$alkyl, which is optionally substituted with 1-6 fluoro,
(3) halo,
(4) oxo,
(5) —$OR^a$,
(6) —CN, and
(7) —$NR^bR^c$,
or wherein two of the substituents on B and the atom(s) to which they are attached are joined to form a ring selected from cyclopropyl, cyclobutyl, cyclopentyl, cyclohexyl, phenyl, naphthyl, thiazolyl, thiazolinyl, oxazolyl, oxazolinyl, imidazolyl, imidazolinyl, imidazolidinyl, isoxazolyl, pyrazolyl, triazolyl, pyridinyl, pyrimidinyl, pyrazinyl, azetidinyl, pyrrolidinyl, piperidinyl, tetrahydrofuranyl, tetrahydropyranyl, and piperazinyl, which ring is optionally substituted with 1-5 substituents each independently selected from —$C_{1-6}$alkyl (which is optionally substituted with 1-3 substituents each independently selected from the group consisting of halo and —$OR^a$), —$C_{3-6}$cycloalkyl, halo, —$SO_2R^d$, —$OR^a$, oxo, —CN and —$NR^bR^c$.

In a subclass of the invention, B is 2-oxopiperidinyl, which is optionally substituted with 1-7 substituents each independently selected from the group consisting of:
(1) —$C_{1-6}$alkyl, which is optionally substituted with 1-7 substituents each independently selected from the group consisting of halo and hydroxy,
(2) phenyl, which is optionally substituted with 1-5 substituents each independently selected from the group consisting of —$C_{1-6}$alkyl (which is optionally substituted with 1-6 fluoro), halo, and hydroxy,
(3) halo, and
(4) oxo.

In another subclass of the invention, B is $C_{3-10}$cycloalkyl, which is optionally substituted with 1-7 substituents each independently selected from the group consisting of:
(1) —$C_{1-6}$alkyl, which is optionally substituted with 1-7 substituents each independently selected from the group consisting of halo and hydroxy,
(2) phenyl, which is optionally substituted with 1-5 substituents each independently selected from the group consisting of:
 (a) —$C_{1-6}$alkyl which is optionally substituted with 1-6 fluoro,
 (b) halo, and
 (c) hydroxy,
(3) halo,
(4) —CN, and
(5) —$NR^bR^c$,
or wherein two of the substituents on B and the atom(s) to which they are attached are joined to form a ring selected from phenyl, imidazolyl, isoxazolyl, oxazolyl, pyridinyl, pyrimidinyl, and piperidinyl, which ring is optionally substituted with 1-3 substituents each independently selected from —$C_{1-6}$alkyl (which is optionally substituted with 1-3 halo), —$OR^a$, —CN, and —$NR^bR^c$.

In a class of the invention $A^1$ is selected from a bond or —$CR^8R^9$—. In a subclass of the invention, $A^1$ is $CH_2$. In a subclass of the invention, $A^1$ is a bond.

In a class of the invention $A^2$ is selected from a bond or —$CR^8R^9$—. In a subclass of the invention, $A^2$ is $CH_2$. In a subclass of the invention, $A^2$ is a bond.

In a class of the invention, $A^5$ is a bond.

In a class of the invention, $A^6$ is selected from: —O—, —$CR^{6a}R^{6b}$—, —$CR^{6a}H$—, or —$CH_2$—. In a subclass of the invention, $A^6$ is —O—. In another subclass of the invention, $A^6$ is —$CR^{6a}R^{6b}$—. In another subclass of the invention, $A^6$ is —$CR^{6a}H$—. In another subclass of the invention, $A^6$ is $CF_2$. In another subclass of the invention, $A^6$ is —$CH(CH_3)$—.

In a class of the invention, $A^7$ is selected from: —O—, —$CR^{6a}R^{6b}$—, —$CR^{6a}H$—, —$CH_2$—, or a bond. In a subclass of the invention, $A^7$ is —O—. In another subclass of the invention, $A^7$ is —$CR^{6a}R^{6b}$—. In another subclass of the invention, $A^7$ is —$CH_2$—. In another subclass of the invention, $A^7$ is a bond.

In a class of the invention, $A^8$ is selected from: —O—, —$CR^{6a}R^{6b}$—, —$CR^{6a}H$—, or —$CH_2$—. In a subclass of the invention, $A^8$ is —O—. In another subclass of the invention, $A^8$ is —$CR^{6a}R^{6b}$. In another subclass of the invention, $A^8$ is —$CR^{6a}H$—. In another subclass of the invention, $A^8$ is —$CH_2$—. In another subclass of the invention, $A^8$ is —CH($CH_3$)—.

In a class of the invention, at least one of $A^6$, $A^7$, and $A^8$ is selected from: —$CR^{6a}R^{6b}$—, —$CR^{6a}H$—, or —O—.

In a class of the invention, $G^1$ is —$C(R^{2a})$=, $G^2$ is —$C(R^{2b})$=, $G^3$ is —N= or —($N^+$—$O^-$)=. In another class of the invention $G^1$ is —$C(R^{2a})$=, $G^2$ is —$C(R^{2b})$=, $G^3$ is —$C(R^{2c})$=.

In a class of the invention, J is =$C(R^{3a})$—. In a class of the invention, J is $N(R^b)$—.

In a class of the invention, Y is =$C(R^{3b})$—. In another class of the invention, Y is —C(=O).

Reference to the preferred classes and subclasses set forth above is meant to include all combinations of particular and preferred groups unless stated otherwise.

Specific embodiments of the present invention include, but are not limited to: N-[(3S,5S,6R)-6-Methyl-2-oxo-5-phenyl-1-(2,2,2-trifluoroethyl)piperidin-3-yl]-2'-oxo-1',2'-dihydro-3H-spiro[1-benzofuran-2,3'-pyrrolo[2,3-b]pyridine]-5-carboxamide; 3,3-Difluoro-N-[(3S,5S,6R)-6-methyl-2-oxo-5-phenyl-1-(2,2,2-trifluoroethyl)piperidin-3-yl]-2'-oxo-1,1',2',3-tetrahydrospiro[indene-2,3'-pyrrolo[2,3-b]pyridine]-5-carboxamide; (R)—N-((3S,5S,6R)-6-Methyl-2-oxo-5-phenyl-1-(2,2,2-trifluoroethyl)piperidin-3-yl)-2'-oxo-1',2'-dihydro-3H-spiro[furo[2,3-b]pyridine-2,3'-pyrrolo[2,3-b]pyridine]-5-carboxamide; (S)—N-((3S,5S,6R)-6-Methyl-2-oxo-5-phenyl-1-(2,2,2-trifluoroethyl)piperidin-3-yl)-2'-oxo-1',2'-dihydro-3H-spiro[furo[2,3-b]pyridine-2,3'-pyrrolo[2,3-b]pyridine]-5-carboxamide; (1S,2R)-1-Methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide; (1R,2S)-1-Methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide; (1R,2R)-1-Methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide; (1S,2S)-1-Methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide; or a pharmaceutically acceptable salt thereof.

The invention also encompasses a pharmaceutical composition which comprises an inert carrier and the compound of Formula I, or a pharmaceutically acceptable salt thereof.

The invention also encompasses a method of treating headache in a mammalian patient in need of such treatment, which comprises administering to the patient a therapeutically effective amount of the compound of Formula I, or a pharmaceutically acceptable salt thereof. In a specific embodiment of the invention, the headache is migraine headache.

The invention also encompasses the use of a compound of Formula I, or a pharmaceutically acceptable salt thereof, and a pharmaceutically acceptable carrier, for the manufacture of a medicament for the treatment of headache. In a specific embodiment of the invention, the headache is migraine headache.

The invention is also directed to medicaments or pharmaceutical compositions for treating diseases or disorders in which CGRP is involved, such as migraine, which comprise a compound of Formula I, or a pharmaceutically acceptable salt thereof, and a pharmaceutically acceptable carrier.

The invention is also directed to the use of a compound of Formula I for treating diseases or disorders in which CGRP is involved, such as migraine.

The invention is further directed to a method for the manufacture of a medicament or a composition for treating diseases or disorders in which CGRP is involved, such as migraine, comprising combining a compound of Formula I with one or more pharmaceutically acceptable carriers.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —$CH_2C(O)$— groups (keto forms) may undergo tautomerism to form hydroxyl —CH=C(OH)— groups (enol forms). Both keto and enol forms are included within the scope of the present invention.

When any variable (e.g. $R^a$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

As used herein, "alkyl" is intended to mean linear or branched structures having no carbon-to-carbon double or triple bonds. Thus, $C_{1-4}$alkyl is defined to identify the group as having 1, 2, 3 or 4 carbons in a linear or branched arrangement, such that $C_{1-4}$alkyl specifically includes, but is not limited to, methyl, ethyl, n-propyl, iso-propyl, n-butyl, iso-butyl and tert-butyl.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

As appreciated by those of skill in the art, "halo" or "halogen" as used herein is intended to include chloro (Cl), fluoro (F), bromo (Br) and iodo (I).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as CGRP receptor antagonists makes them useful pharmacological agents for disorders that involve CGRP in humans and animals, but particularly in humans.

The compounds of the present invention may have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; obesity; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In an embodiment of the invention the present compounds may be used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 µL) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY (Assay A): Cells expressing recombinant human CL receptor/RAMP1 were washed with PBS and harvested in harvest buffer containing 50 mM HEPES, 1 mM EDTA and Complete™ protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 µg of membranes were incubated in 1 mL binding buffer (10 mM HEPES, pH 7.4, 5 mM MgCl$_2$, and 0.2% BSA) for 3 h at room temperature containing 10 pM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4, and 5 mM MgCl$_2$). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{Y_{min} + (Y_{max} - Y_{min})(100 - \% \, I_{max}/100)}{1 + ([Drug]/K_i(1 + [Radiolabel]/K_d)^{nH}}$$

Where Y is observed CPM bound, Y$_{max}$ is total bound counts, Y$_{min}$ is non specific bound counts, (Y$_{max}$-Y$_{min}$) is specific bound counts, % I$_{max}$ is the maximum percent inhibition, % I min is the minimum percent inhibition, radiolabel is the probe, and the K$_d$ is the apparent dissociation constant for the radioligand for the receptor as determined by hot saturation experiments.

RECOMBINANT RECEPTOR FUNCTIONAL ASSAY (Assay B): Cells were resuspended in DMEM/F12 (Hyclone) supplemented with 1 g/L BSA and 300 µM isobutyl-methylxanthine. Cells were then plated in a 384-well plate (Proxiplate Plus 384; 509052761; Perkin-Elmer) at a density of 2,000 cells/well and incubated with antagonist for 30 min at 37° C. Human α-CGRP was then added to the cells at a final concentration of 1.2 nM and incubated an additional 20 min at 37° C. Following agonist stimulation, the cells were processed for cAMP determination using the two-step procedure according to the manufacturer's recommended protocol (HTRF cAMP dynamic 2 assay kit; 62AM4PEC; Cisbio). Raw data were transformed into concentration of cAMP using a standard curve then dose response curves were plotted and inflection point (IP) values were determined.

RECOMBINANT RECEPTOR FUNCTIONAL ASSAY (Assay C): Cells were resuspended in DMEM/F12 (Hyclone) supplemented with 1 g/L BSA and 300 µM isobutyl-methylxanthine. Cells were then plated in a 384-well plate (Proxiplate Plus 384; 509052761; Perkin-Elmer) at a density of 3,500 cells/well and incubated with antagonist for 30 min at 37° C. Human α-CGRP was then added to the cells at a final concentration of 1 nM and incubated an additional 20 min at 37° C. Following agonist stimulation, the cells were processed for cAMP determination using the two-step procedure according to the manufacturer's recommended protocol (HTRF cAMP dynamic 2 assay kit; 62AM4PEC; Cisbio). Raw data were transformed into concentration of cAMP using a standard curve then dose response curves were plotted and inflection point (IP) values were determined.

Representative $IC_{50}$ values in the recombinant receptor functional assays for exemplary compounds of the invention are provided in the table below:

| Example | Assay | $IC_{50}$ (nM) |
| --- | --- | --- |
| 3 isomer A | B | 129 |
| 3 isomer B | B | 1.5 |
| 4A | C | 6.7 |
| 4B | C | 0.68 |
| 5A | C | 5.4 |
| 5B | C | 0.050 |

The following abbreviations are used throughout the text:
Me: methyl
Et: ethyl
t-Bu: tert-butyl
Bu: butyl
i-Pr: isopropyl
Ar: aryl
Ph: phenyl
Bn: benzyl
Py: pyridyl
Ac: acetylate
OAc: acetate
DCE: 1,2-dichloroethane
TFA: trifluoroacetic acid
TEA: triethylamine
Boc: tert-butoxycarbonyl
BOP: (benzotriazol-1-yloxy)tris(dimethylamino)phosphonium hexafluorophosphate
DIEA: N,N-diisopropylethylamine
HOBT: 1-hydroxybenzotriazole
EDC: N-(3-dimethylaminopropyl)-N'-ethylcarbodiimide hydrochloride
PyCIU: chlorodipyrrolidinocarbenium
n-BuLi: n-butyllithium
n-HexLi n-hexyllithium
HATU: O-(7-azabenzotriazol-1-yl)-N,N,N'N'-tetramethyluronium hexafluorophosphate
EDTA: ethylenediaminetetraacetic acid
DMF: N,N-dimethylformamide
HMDS: hexamethyldisilazane
THF: tetrahydrofuran
DMSO: dimethylsulfoxide
SEM: 2-trimethylsilylethoxymethyl
SEMCl: 2-trimethylsilylethoxymethyl chloride
PBPB: pyridinium bromide perbromide
DMEM: Dulbecco's Modified Eagle Medium (High Glucose)
FBS: fetal bovine serum
BSA: bovine serum albumin
PBS: phosphate-buffered saline
HEPES: N-(2-hydroxyethyl)piperazine-N'-(2-ethanesulfonic acid)
SM: starting material
min: minutes
h: hours
aq: aqueous
HPLC: high performance liquid chromatography
LCMS: liquid chromatography-mass spectrometry
SFC: supercritical fluid chromatography
NMP: 1-methyl-2-pyrrolidinone
MTBE: methyl tert-butyl ether
DMA: N,N-dimethylacetamide
NBS: N-bromosuccinimide
CAN: ammonium cerium(IV) nitrate
dppf: 1,1'-bis(diphenylphosphino)ferrocene
dba: dibenzylideneacetone
BINAP: 2,2'-bis(diphenylphosphino)-1,1'-binaphthalene
Ms: methanesulfonyl
p-Ts: 4-toluenesulfonyl
trisyl: 2,4,6-triisopropylbenzenesulfonyl
DMAP: 4-(dimethylamino)pyridine
DMAC: N,N-dimethylacetamide
PMBCl: 4-methoxybenzyl chloride
DMPU: N,N'-dimethylpropyleneurea
DIBAL: diisobutylaluminum hydride
DIPEA: N,N-diisopropylethylamine
TCCA: trichloroisocyanuric acid
DAST: (diethylamino)sulfur trifluoride
DBU: 1,8-diazabicyclo[5.4.0]undec-7-ene
AIBN: 2-2'-azobisisobutyronitrile
DDQ: 2,3-dichloro-5,6-dicyano-1,4-benzoquinone Methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

Reaction Schemes

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Scheme 1 illustrates a route to 3-aminopiperidinone intermediates of type 1.5 which may be used to prepare compounds of the present invention. Aryl acetone 1.1 can be alkylated using the iodoalanine derivative 1.2 under basic conditions to provide keto ester 1.3. Reductive amination followed by cyclization and epimerization provides primarily cis-substituted lactam 1.4 as a racemic mixture. Chiral resolution using normal-phase liquid chromatography, for example, and removal of the Boc protecting group with HCl in EtOAc furnishes 3-aminopiperidinone 1.5 as a hydrochloride salt.

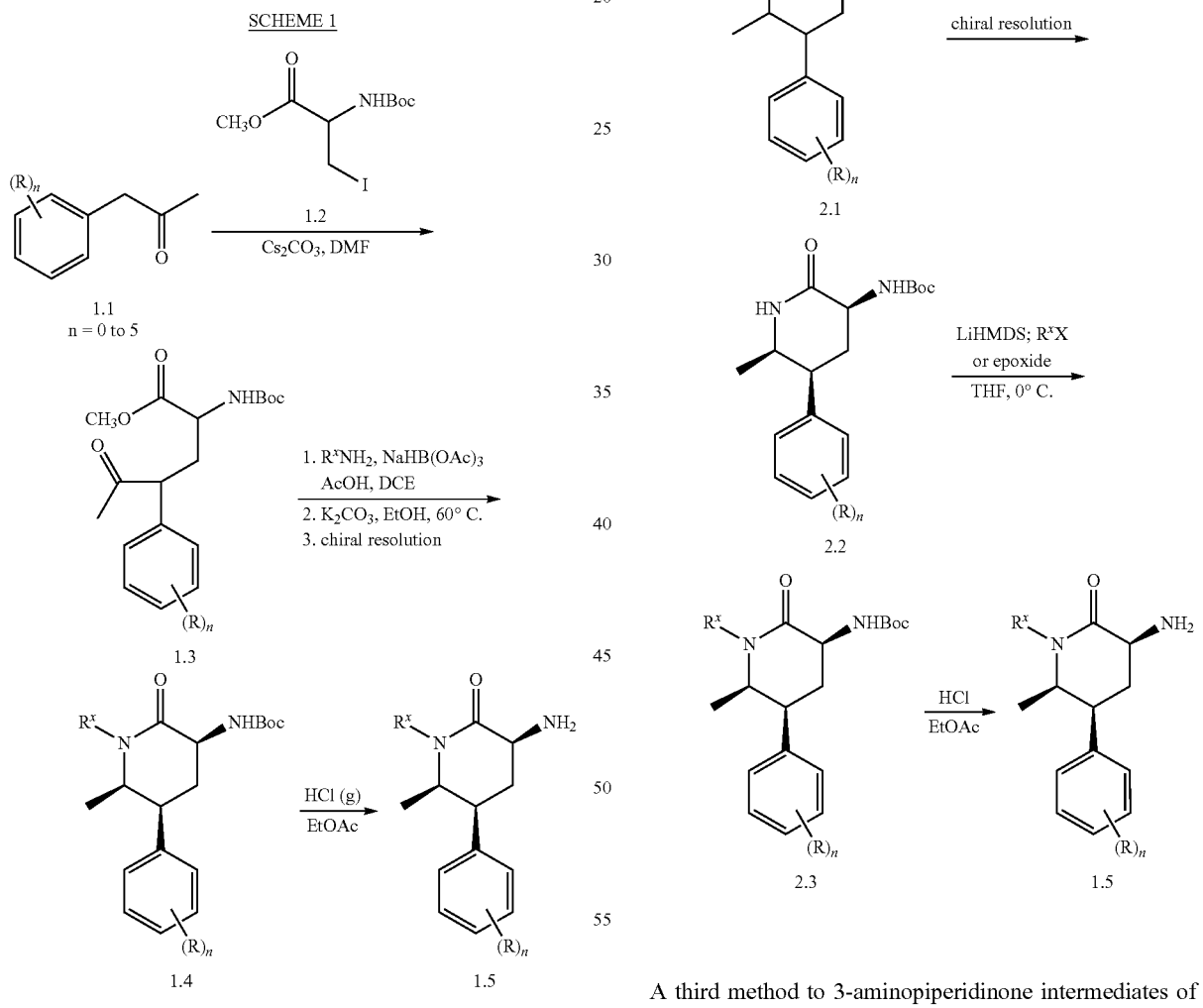

An alternative sequence to 3-aminopiperidinone intermediates of type 1.5 is shown in Scheme 2. Reductive amination of keto ester 1.3 with ammonia followed by epimerization provides 2.1 as a mostly cis-substituted racemic mixture. Chiral resolution of the enantiomers provides 2.2. N-Alkylation with LiHMDS as base, for example, and an alkyl halide or epoxide affords 2.3. Removal of the Boc protecting group with HCl then affords 1.5 as a hydrochloride salt.

A third method to 3-aminopiperidinone intermediates of type 1.5 is shown in Scheme 3. N-Alkylation of 5-bromo-6-methylpyridin-2(1H)-one (3.1) using cesium carbonate as base and an alkyl halide followed by nitration provides 3.2. Palladium-catalyzed cross-coupling with an aryl boronic acid then affords 3.3. Hydrogenation using platinum oxide under acidic conditions and chiral resolution of the mostly cis-substituted racemic product mixture provides 1.5 as a single enantiomer.

SCHEME 3

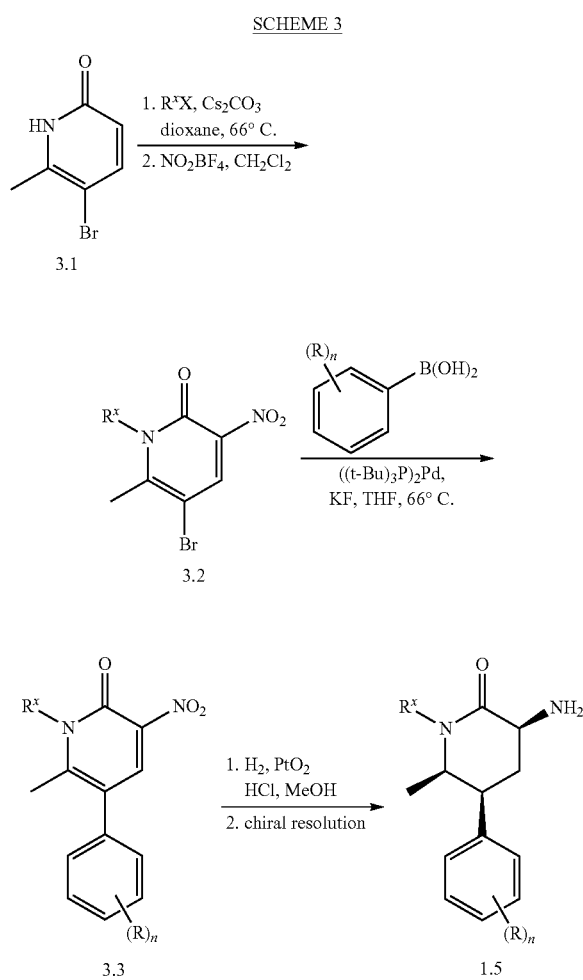

A synthetic route to 3-aminopiperidinone intermediates of type 4.4 is shown in Scheme 4. Aryl acetonitrile 4.1 can be alkylated using the iodoalanine derivative 1.2 under basic conditions to provide cyano ester 4.2. Reductive cyclization using hydrogen and palladium hydroxide on carbon or Raney nickel, epimerization, and chiral resolution affords cis lactam 4.3 as a single enantiomer. N-Alkylation and removal of the Boc protecting group then provides 4.4 as a hydrochloride salt.

SCHEME 4

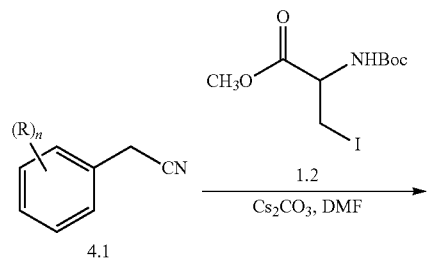

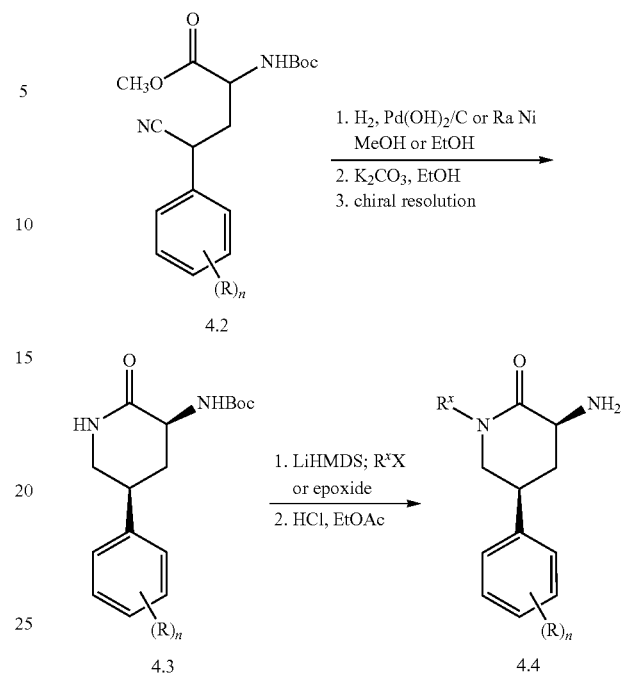

Scheme 5 illustrates an alternative route to 3-aminopiperidinone intermediates of type 4.4. The arylacetonitrile 5.1 may be condensed with acrylate 5.2 at elevated temperature to give the 4-cyanobutanoate ester 5.3. Hydrogenation of nitrile 5.3 using Raney nickel catalyst and an ethanolic solution of ammonia affords the corresponding amine product, which typically cyclizes in situ to provide piperidinone 5.4. N-Alkylation of lactam 5.4 may be accomplished by a variety of methods known to those skilled in the art of organic synthesis, the exact choice of conditions being influenced by the nature of the alkylating agent, $R^1X$. Electrophilic azidation of the resulting substituted lactam 5.5 can be accomplished using similar methodology to that described by Evans and coworkers (Evans et al. (1990) *J. Am. Chem. Soc.* 112, 4011-4030) to provide the azide 5.6 as a mixture of diastereoisomers, which can be separated by chromatography. The desired cis diastereomer of azide 5.6 may be reduced by catalytic hydrogenation in the presence of di-tert-butyl dicarbonate to give the corresponding Boc-protected amine 5.7, and separation of the enantiomers using chiral HPLC or SFC leads to the (3S,5S)-isomer 5.8. Finally, standard deprotection affords the desired 3-aminopiperidinone intermediate 4.4 as a hydrochloride salt.

SCHEME 5

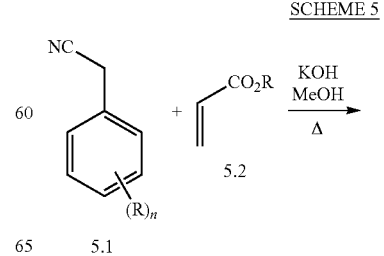

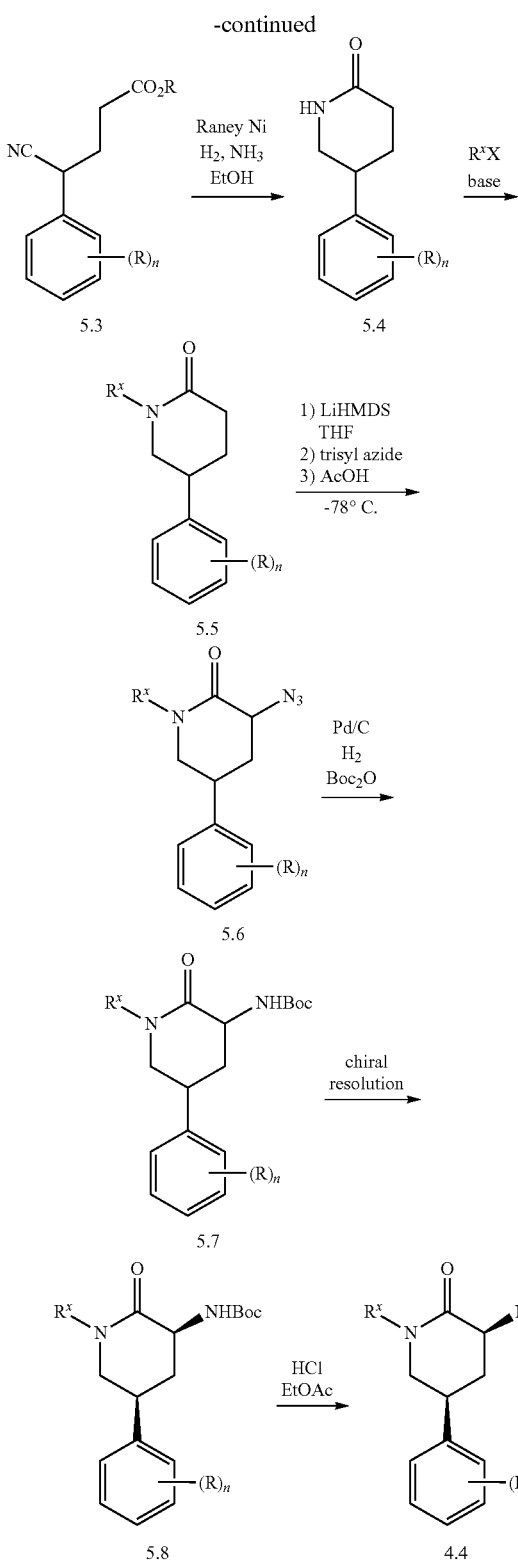

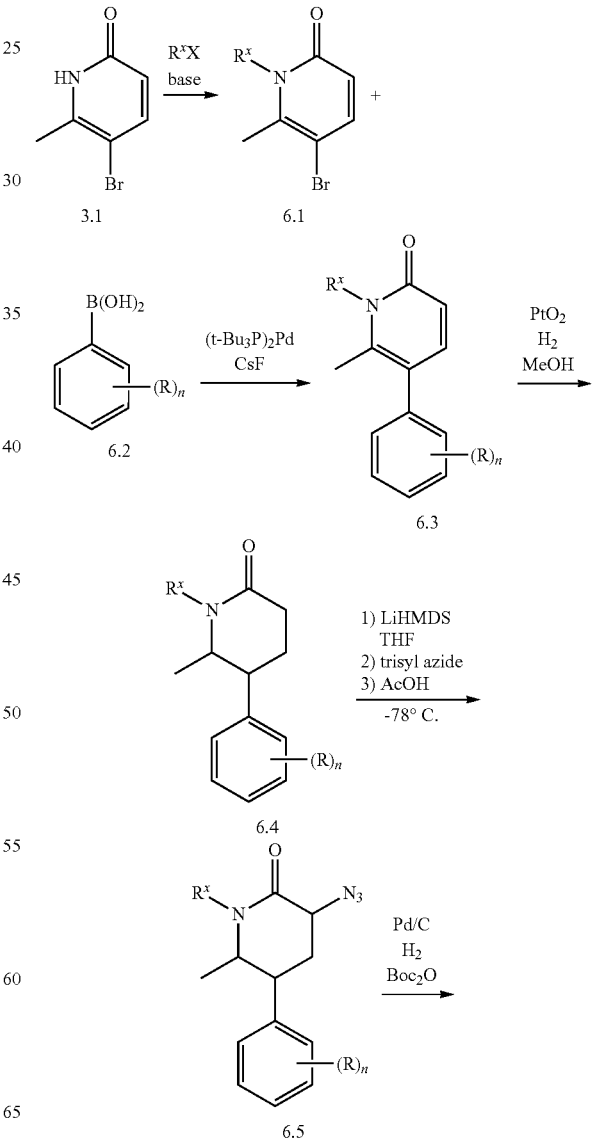

be hydrogenated using, for example, platinum(IV) oxide catalyst to afford the corresponding 5-arylpiperidinone 6.4, which is usually obtained as predominantly the cis isomer. Further elaboration of piperidinone 6.4 may be achieved using analogous methodology to that described in Scheme 5. Specifically, electrophilic azidation followed by one-pot reduction and Boc protection leads to carbamate 6.6, and the desired enantiomer may be obtained using chiral chromatography. In some cases, the desired diastereomer of azide 6.5 may be isolated as a racemic mixture of the (3S,5S,6R)- and (3R,5R,6S)-isomers following silica gel chromatography of the crude product, and this mixture may be elaborated as outlined in Scheme 6. In other cases, it may be advantageous to take a mixture of diastereomers of azide 6.5 forward to the corresponding carbamate 6.6. The mixture of carbamate 6.6 diastereomers may be epimerized under basic conditions, such as potassium carbonate in EtOH, to afford a mixture that is significantly enriched in the desired (3S,5S,6R)- and (3R, 5R,6S)-isomers, further purification may be employed to obtain the enantiomer of interest as outlined herein.

SCHEME 6

Another approach to 3-aminopiperidinone intermediates of interest, which is particularly useful for preparing 3-amino-6-methyl-5-arylpiperidin-2-ones such as 1.5, is outlined in Scheme 6. The pyridin-2(1H)-one 3.1 may be converted to the N-substituted pyridinone 6.1 by treatment with a suitable electrophile ($R^1X$) under basic conditions. Pyridinone 6.1 can then be subjected to Suzuki coupling with the boronic acid 6.2, and the resulting 5-arylpyridinone 6.3 may

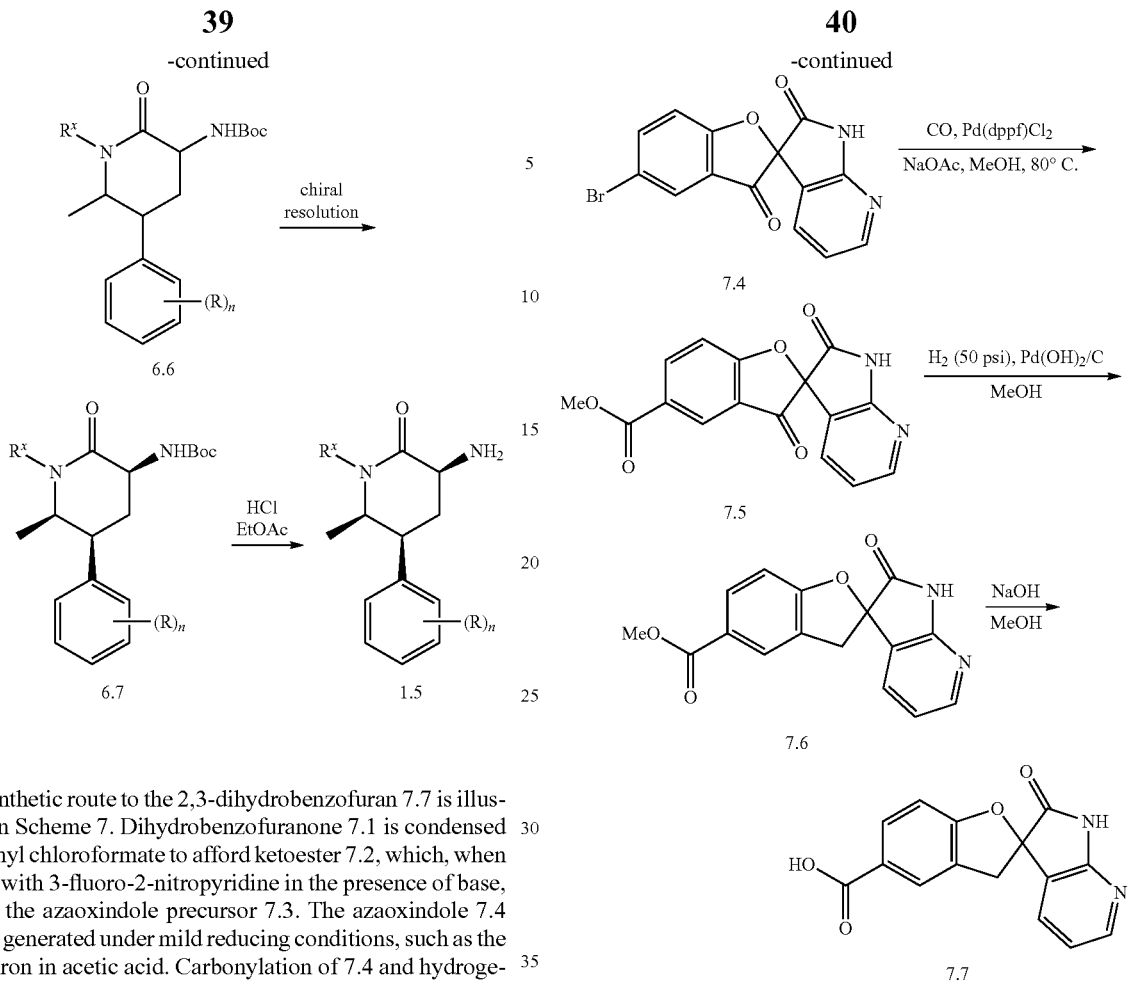

A synthetic route to the 2,3-dihydrobenzofuran 7.7 is illustrated in Scheme 7. Dihydrobenzofuranone 7.1 is condensed with ethyl chloroformate to afford ketoester 7.2, which, when treated with 3-fluoro-2-nitropyridine in the presence of base, affords the azaoxindole precursor 7.3. The azaoxindole 7.4 may be generated under mild reducing conditions, such as the use of iron in acetic acid. Carbonylation of 7.4 and hydrogenation of the product 7.5 to remove the ketone carbonyl provides ester 7.6, which undergoes hydrolysis with sodium hydroxide to furnish carboxylic acid 7.7

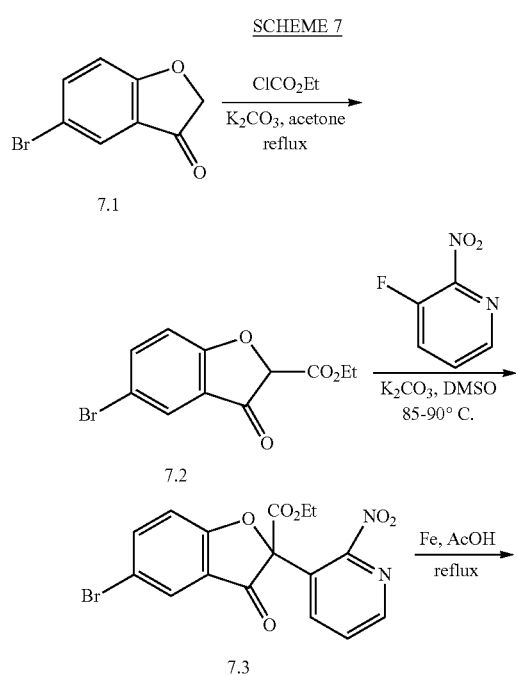

As depicted in Scheme 8, the known bromomethylnitrobenzoyl chloride 8.1 (described in Pifferi et al. (1966) *Tetrahedron* 22, 2107) may be condensed with intermediate 8.2 (such as the SEM-protected azaoxindole described in WO2008/020902) to give rise to ketone 8.3. Treatment with DAST affords the difluoro derivative 8.4, and reduction of the nitro group under standard hydrogenation conditions provides aniline 8.5. Additionally, the ketone intermediate 8.3 may be further elaborated to other intermediates including, but not limited to, alcohols or amines, which may be used in the preparation of compounds described in the present invention. Diazotization of aniline 8.5 followed by treatment with potassium iodide may yield the corresponding iodide 8.6, which can undergo carbonylation in methanol to afford ester 8.7. Standard saponification conditions may then produce carboxylic acid 8.8 for use in the preparation of compounds described in the present invention.

SCHEME 8

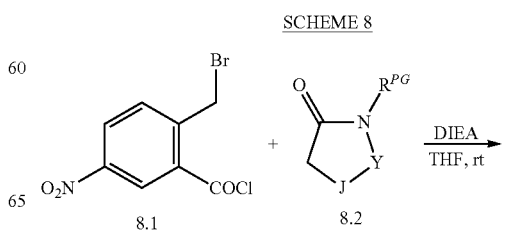

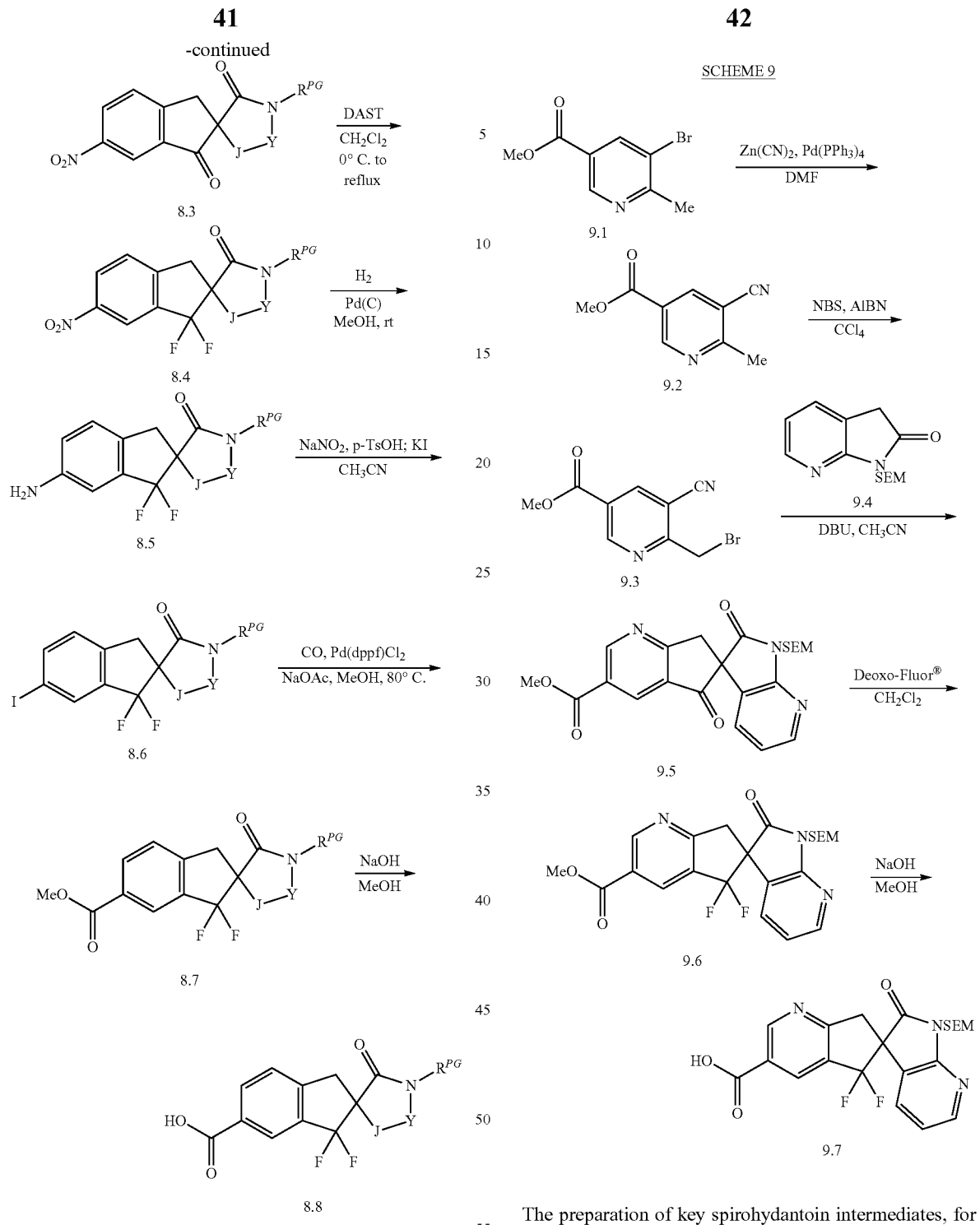

Scheme 9 depicts a route to the related carboxylic acid 9.7. Palladium-catalyzed cyanation of bromopyridine 9.1 and subsequent benzylic bromination of 9.2, using N-bromosuccinimide in carbon tetrachloride, provides 9.3. Condensation of 9.3 with azaoxindole 9.4 (prepared according to the procedures described in WO2008/020902) furnishes the spirocyclic ketone 9.5. Treatment of 9.5 with Deoxo-Fluor® followed by hydrolysis of the product ester 9.6 provides carboxylic acid 9.7.

The preparation of key spirohydantoin intermediates, for use in the preparation of the compounds of the present invention, is illustrated in Scheme 10. Ketone 10.1 (for example 1-methyl-1,3-dihydro-2H-inden-2-one) may be converted to the corresponding spirohydantoin 10.2 utilizing standard Bucherer-Bergs methodology. Nitration and reduction of the resulting nitrobenzene 10.3 affords aniline 10.4, which may be further elaborated in analogy with the previous schemes. Diazotization, followed by treatment with potassium iodide, provides iodide 10.5, which can undergo carbonylation in methanol to afford ester 10.6. Saponification may then produce carboxylic acid 10.7 for use in the preparation of compounds described in the present invention.

SCHEME 10

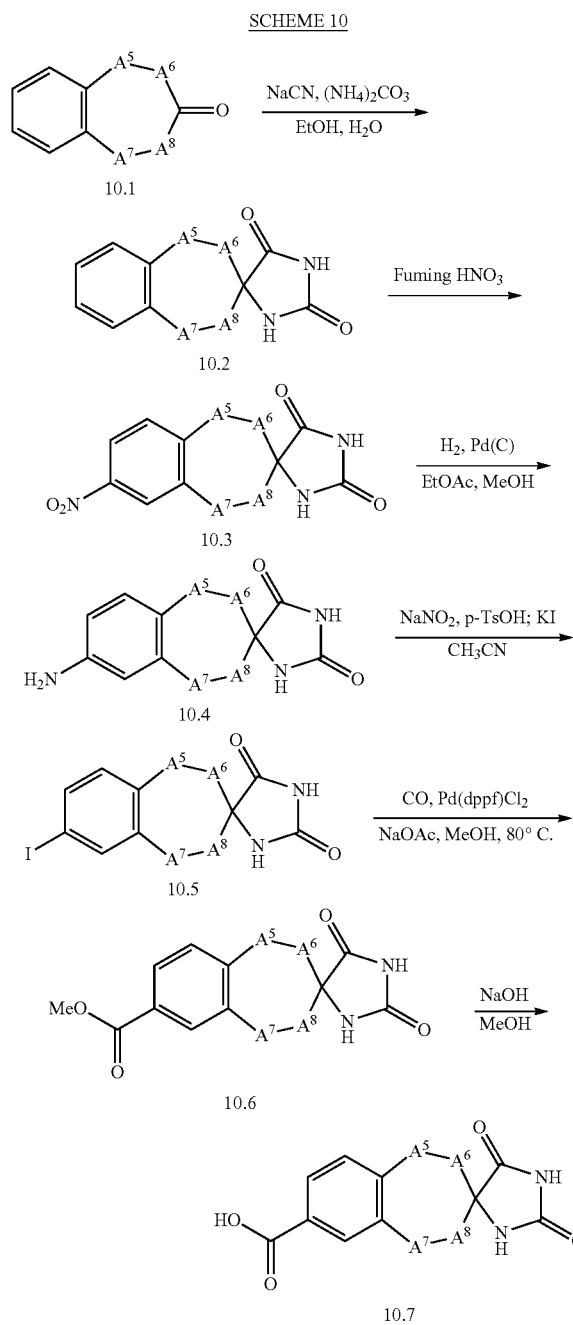

SCHEME 11

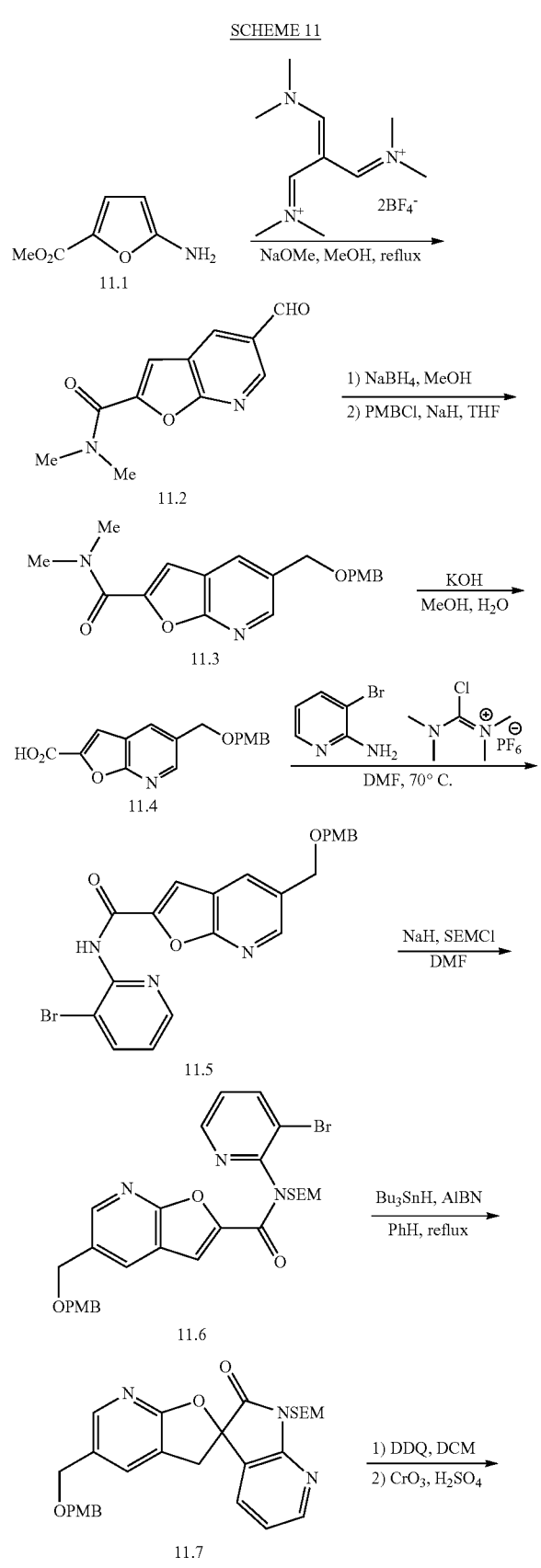

Scheme 11 depicts a synthetic route to the furo[2,3-b]pyridine carboxylic acid 11.8. Methyl 5-aminofuran-2-carboxylate 11.1 is condensed with 2-[(dimethylamino)methylene]-1,3-bis(dimethyliminio)propane bis(tetrafluoroborate) in the presence of sodium methoxide to afford aldehyde 11.2. Reduction with sodium borohydride and alkylation of the resulting alcohol with 4-methoxybenzyl chloride provides ether 11.3. Hydrolysis of the dimethylamide followed by coupling of carboxylic acid 11.4 with 3-bromo-2-amino pyridine yields amide 11.5, which is protected with SEMCl to afford 11.6. Heating with tributyltin hydride and catalytic AIBN promotes cyclization to 11.7. Cleavage of the PMB protecting group with DDQ followed by oxidation with Jones reagent then provides 11.8.

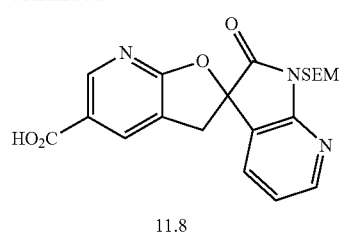 [SMILES: C[Si](C)(C)CCOCN1C(=O)C2(Cc3cc(C(=O)O)cnc3O2)c2cccnc21]

11.8

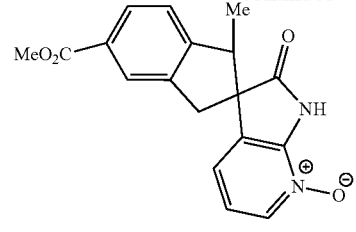

12.5

A synthetic sequence to spiroindane 12.6 is illustrated in Scheme 12. Alkylation of 12.1 with the sodium anion of tert-butyl 2-(diethoxyphosphoryl)acetate affords 12.2. Olefination with paraformaldyhyde and potassium carbonate followed by removal of the tert-butyl group with TFA provides carboxylic acid 12.3. Coupling with 2-amino-3-bromopyridine 1-oxide gives amide 12.4 which can undergo a palladium-catalyzed tandem Heck reaction in analogy with literature precedent (Ruck, R. T. et al *Angew. Chem. Int. Ed.* 2008, 47, 4711-4714) to afford 12.5 as a mixture of diastereomers. Reduction of the N-oxide with phosphorous tribromide and saponification then provides 12.6.

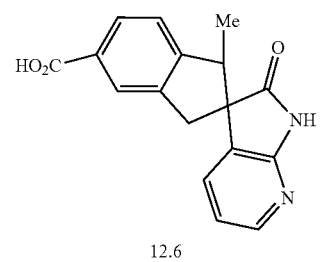

12.6

Scheme 13 illustrates conditions that can be used for the coupling of 3-aminopiperidinone intermediates, such as 13.1, and carboxylic acid intermediate 13.2, to produce, in this instance, the amide 13.3. These standard coupling conditions are representative of the methods used to prepare the compounds of the present invention.

SCHEME 12

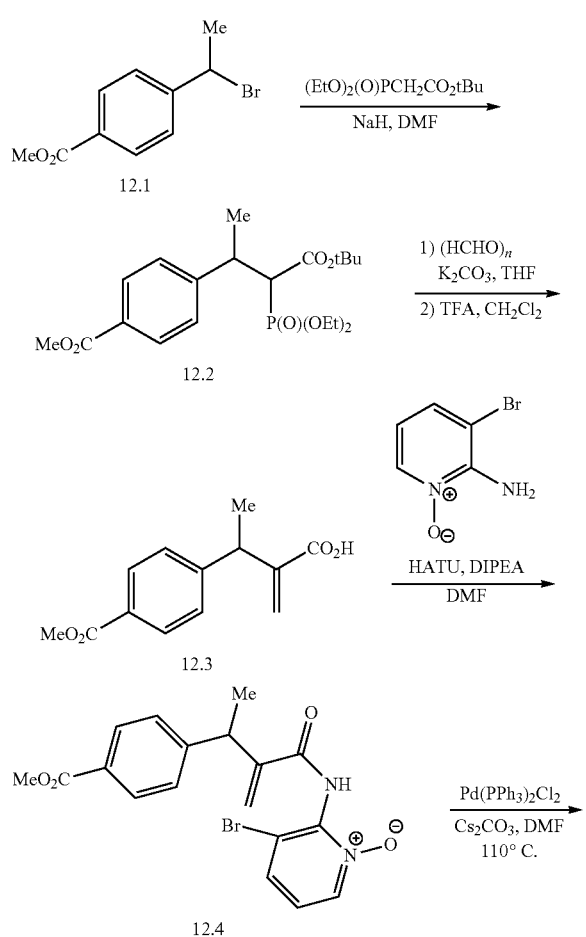

SCHEME 13

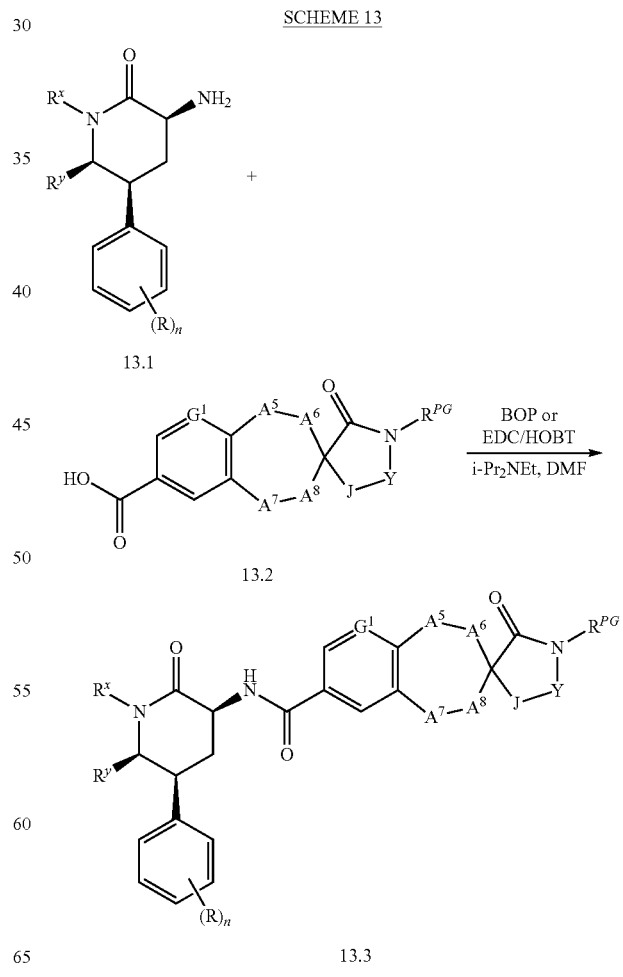

In some cases, alternative coupling conditions may be used to prepare the compounds of the present invention. In some cases, various protecting group strategies familiar to one skilled in the art of organic synthesis may be employed to allow preparation of a particular compound of the present invention.

It is understood that alternative methodologies may also be employed in the synthesis of these key intermediates. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, appropriate protecting group strategies may be used.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

Intermediate 1

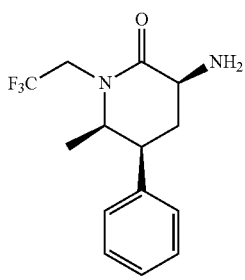 [SMILES: C[C@@H]1[C@H](c2ccccc2)C[C@H](N)C(=O)N1CC(F)(F)F]

(3S,5S,6R)-3-Amino-6-methyl-5-phenyl-1-(2,2,2-trifluoroethyl)piperidin-2-one

Step A: Methyl 2-[(tert-butoxycarbonyl)amino]-4-(3-chlorophenyl)-5-oxohexanoate

A mixture of cesium carbonate (9.80 g, 30.1 mmol) and methyl N-(tert-butoxycarbonyl)-3-iodo-D-alaninate (9.90 g, 30.1 mmol) in DMF (75 mL) was stirred at ambient temperature for 45 min before 1-(3-chlorophenyl)propan-2-one (6.09 g, 36.1 mmol) and additional cesium carbonate (9.80 g, 30.1 mmol) were added. The resulting mixture was stirred for 2.5 h. The majority of the DMF was then removed under reduced pressure at a bath temperature of <40° C. The concentrated mixture was partitioned between water (500 mL) and ethyl acetate (2×200 mL). The combined organic layers were washed with brine, dried over sodium sulfate and concentrated in vacuo to give the title compound as a 1:1 racemic mixture of diastereomers, which was used without further purification. MS: m/z=314.1 (M−t-Bu+1).

Step B: tert-Butyl[(3S,5S,6R)-5-(3-chlorophenyl)-6-methyl-2-oxo-1-(2,2,2-trifluoroethyl)piperidin-3-yl] carbamate A slurry of methyl 2-[(tert-butoxycarbonyl)amino]-4-(3-chlorophenyl)-5-oxohexanoate as a 1:1 racemic mixture of diastereomers (11.1 g, 30.0 mmol), 2,2,2-trifluoroethylamine (9.59 mL, 120 mmol), acetic acid (10.3 mL, 180 mmol), sodium triacetoxyborohydride (25.4 g, 120 mmol), and flame-dried 4 Å molecular sieves (50 g) in 1,2-dichloroethane (300 mL) was stirred at ambient temperature for 8 h. Additional 2,2,2-trifluoroethylamine (9.59 mL, 120 mmol), acetic acid (10.3 mL, 180 mmol), and sodium triacetoxyborohydride (25.4 g, 120 mmol) were added and stirring was continued for 20 h. The reaction mixture was diluted with dichloromethane (200 mL) then poured into water (500 mL). Molecular sieves were removed by filtration, and the organic layer was washed with water (3×500 mL), dried over sodium sulfate, and concentrated in vacuo. A solution of the residue in ethanol (200 mL) was stirred in the presence of solid potassium carbonate (12.4 g, 90 mmol) at 60° C. for 2 h, then ambient temperature for 16 h. The bulk of the ethanol was removed under reduced pressure and the remaining slurry was then partitioned between water (500 mL) and ethyl acetate (300 mL). The organic layer was washed with brine, dried over sodium sulfate and concentrated in vacuo. The residue was crystallized from a 2:1 mixture of hexane and ethyl ether to give the title compound as a racemate. The enantiomers were separated using normal-phase HPLC using a ChiralPak® AD column, eluting with 40% hexane in ethanol initially, stepping to 20% hexane in ethanol (0.1% diethylamine used as a modifier) to afford the title compound as the second enantiomer to elute. MS: m/z=421.2 (M+1).

Step C: (3S,5S,6R)-3-Amino-6-methyl-5-phenyl-1-(2,2,2-trifluoroethyl)piperidin-2-one A mixture of tert-butyl [(3S,5S,6R)-5-(3-chlorophenyl)-6-methyl-2-oxo-1-(2,2,2-trifluoroethyl)piperidin-3-yl]carbamate (2.75 g, 6.53 mmol) and 20 wt. % palladium hydroxide on carbon (~50 wt. % wet, 700 mg, 0.50 mmol) in methanol (100 mL) was stirred under a hydrogen balloon at ambient temperature for 16 h. The catalyst was removed by filtration through Celite® and washed thoroughly with methanol and ethyl acetate. Following concentration of the filtrate, a solution of the residue in ethyl acetate (100 mL) pre-cooled to 0° C. was sparged with HCl gas for ~1 min. The ice-bath was removed and the acidic solution was allowed to warm to ambient temperature as stirring was continued for 2 h. The mixture was then concentrated to dryness in vacuo to afford the title compound as a hydrochloride salt. HRMS: m/z=287.1361, calculated m/z=287.1366 for $C_{14}H_{18}F_3N_2O$. $^1$H NMR (500 MHz, $CD_3OD$) δ 7.39 (t, 2H, J=7.3 Hz), 7.31 (t, 1H, J=7.3 Hz), 7.27 (d, 2H, J=7.3 Hz), 4.81-4.73 (m, 1H), 4.24 (dd, 1H, J=12.0, 6.8 Hz), 3.94 (p, 1H, J=6.0 Hz), 3.76-3.67 (m, 2H), 2.56 (q, 1H, J=12.7 Hz), 2.42 (m, 1H), 1.00 (d, 3H, J=6.3 Hz).

Intermediate 2

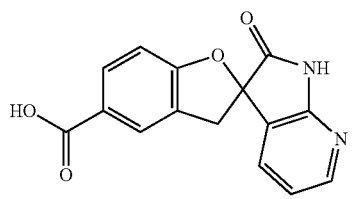 [SMILES: O=C(O)c1ccc2c(c1)CC1(O2)C(=O)Nc2ncccc21]

2'-Oxo-1',2'-dihydro-3H-spiro[benzofuran-2,3'-pyrrolo[2,3-b]pyridine]-5-carboxylic acid Step A: Ethyl 5-bromo-3-oxo-2,3-dihydro-1-benzofuran-2-carboxylate Potassium carbonate (1.66 g, 12 mmol) is added to a solution of 5-bromo-1-benzofuran-3(2H)-one (2.13 g, 10 mmol) in acetone (25 mL). The stirred mixture is treated dropwise with ethyl chloroformate (1.05 mL, 11 mmol). The mixture is then heated at reflux for 18 h. The solids are filtered off and the filtrate concentrated in vacuo. The residue is partitioned between EtOAc and saturated aqueous NaHCO₃. The layers are separated and the organic layer washed with brine, dried (Na₂SO₄), filtered and concentrated in vacuo. The residue is purified by silica gel chromatography (gradient elution with hexanes-EtOAc) to afford the title compound.

Step B: Ethyl 5-bromo-2-(2-nitropyridin-3-yl)-3-oxo-2,3-dihydro-1-benzofuran-2-carboxylate A mixture of ethyl 5-bromo-3-oxo-2,3-dihydro-1-benzofuran-2-carboxylate (1.42 g, 5.0 mmol), 2-nitro-3-fluoropyridine (0.71 g, 5 mmol) and potassium carbonate (0.83 g, 6.0 mmol) in DMSO (15 mL) is heated at 85-90° C. for 18 h. The mixture is cooled to ambient temperature and partitioned between EtOAc and brine. The layers are separated and the aqueous layer is further extracted with EtOAc. The combined organic extracts are dried (Na₂SO₄), filtered and concentrated in vacuo. The residue is purified by silica gel chromatography (gradient elution with hexanes-EtOAc) to afford the title compound.

Step C: 5-Bromo-3H-spiro[1-benzofuran-2,3'-pyrrolo[2,3-b]pyridine]-2',3(1M-dione Ethyl 5-bromo-2-(2-nitropyridin-3-yl)-3-oxo-2,3-dihydro-1-benzofuran-2-carboxylate (305 mg, 0.75 mmol) is dissolved in acetic acid (2 mL). Iron powder (0.21 g, 3.8 mmol) is added and the mixture heated at 100° C. for 1 h. The acetic acid is removed in vacuo and the residue taken up in EtOAc. The solids are filtered off and the filtrate is washed with 1 N HCl (3×) followed by brine. The organic layer is dried (Na₂SO₄), filtered and concentrated in vacuo to give the title compound.

Step D: Methyl 2',3-dioxo-1',2'-dihydro-3H-spiro[benzofuran-2,3'-pyrrolo[2,3-b]pyridine]-5-carboxylate A solution of 5-bromo-3H-spiro[1-benzofuran-2,3'-pyrrolo[2,3-b]pyridine]-2',3(1'H)-dione (300 mg, 0.91 mmol), sodium acetate (149 mg, 1.81 mmol) and dichloro 1,1'-bis(diphenylphosphino)ferrocene palladium(II) dichloromethane adduct (18 mg, 0.023 mmol) in MeOH (5 mL) is pressurized to 120 psi with carbon monoxide and then heated at 80° C. for 12 h with stirring. The reaction mixture is diluted with water (20 mL), and the precipitate collected by filtration, washed with water, and dried under nitrogen atmosphere to give the title compound.

Step E: Methyl 2'-oxo-1',2'-dihydro-3H-spiro[benzofuran-2,3'-pyrrolo[2,3-b]pyridine]-5-carboxylate A mixture of methyl 2',3-dioxo-1',2'-dihydro-3H-spiro[benzofuran-2,3'-pyrrolo[2,3-b]pyridine]-5-carboxylate (200 mg, 0.64 mmol) and 20 wt. % palladium hydroxide on carbon (40 mg) in MeOH (5 mL) is stirred under an atmosphere of hydrogen (50 psi) for 18 h. The reaction mixture is then filtered through a pad of Celite° and the filtrate is concentrated in vacuo. The residue is partitioned between CH₂Cl₂ and saturated aqueous NaHCO₃ solution. The layers are separated and the aqueous layer is further extracted with CH₂Cl₂ (2×). The combined organic extracts are dried (Na₂SO₄), filtered and concentrated in vacuo to afford the title compound.

Step E: 2'-Oxo-1',2'-dihydro-3H-spiro[benzofuran-2,3'-pyrrolo[2,3-b]pyridine]-5-carboxylic acid A mixture of methyl 2'-oxo-1',2'-dihydro-3H-spiro[benzofuran-2,3'-pyrrolo[2,3-b]pyridine]-5-carboxylate (100 mg, 0.34 mmol) and aqueous 6 N sodium hydroxide solution (0.17 mL, 1.0 mmol) in MeOH (5 mL) is heated at reflux for 1 h. The mixture is allowed to cool to ambient temperature before it is acidified to pH ~6 with aqueous 1 N hydrochloric acid solution. The resulting mixture is filtered, and the filtrate is concentrated. The residue is partitioned between water (10 mL) and 2-methyltetrahydrofuran (2-MeTHF, 10 mL). The aqueous layer is extracted with 2-MeTHF (5×10 mL), and the combined organic layers are dried over sodium sulfate and concentrated to provide the title compound.

Intermediate 3

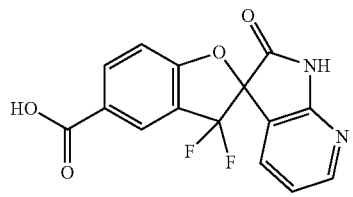 [SMILES: O=C(O)c1ccc2c(c1)C(F)(F)C1(O2)C(=O)Nc2ncccc21]

1,1-Difluoro-2'-oxo-1,1',2',3-tetrahydrospiro[indene-2,3'-pyrrolo[2,3-b]pyridine]-6-carboxylic acid Step A: 6-Nitro-1'-{[2-(trimethylsilyl)ethoxy]methyl}spiro[indene-2,3'-pyrrolo[2,3-b]pyridine]-1,2'(1'H,3H)-dione N,N-Diisopropylethylamine (3.64 mL, 22 mmol) is added to a stirred solution of 1-{[2-(trimethylsilyl)ethoxy]methyl}-1,3-dihydro-2H-pyrrolo[2,3-b]pyridin-2-one (prepared according to the procedures described in WO2008/020902) (2.64 g, 10 mmol) in THF (75 mL) at ambient temperature. To the stirred mixture is added dropwise a solution of 2-(bromomethyl)-5-nitrobenzoyl chloride (3.06 g, 11 mmol) [Pifferi et al. (1966) *Tetrahedron* 22, 2107] in THF (75 mL) and the mixture is then stirred at ambient temperature for 18 h. The mixture is then partitioned between EtOAc and saturated aqueous NaHCO$_3$. The layers are separated and the aqueous layer further extracted with EtOAc. The combined organic extracts are washed with brine, dried (Na$_2$SO$_4$) and concentrated in vacuo. The residue is purified by silica gel chromatography (gradient elution with hexanes-EtOAc) to afford the title compound.

Step B: 1,1-Difluoro-6-nitro-1,3-dihydrospiro[indene-2,3'-pyrrolo[2,3-b]pyridin]-2'(1'H)-one A solution of 6-nitro-1'-{[2-(trimethylsilyl)ethoxy]methyl}spiro[indene-2,3'-pyrrolo[2,3-b]pyridine]-1,2'(1'H,3H)-dione (0.85 g, 2.0 mmol) in CH$_2$Cl$_2$ (10 mL) is cooled to 0° C. and treated with DAST (0.80 mL, 6.5 mmol). The resulting mixture is allowed to warm to ambient temperature and then heated at reflux for 18 h. The reaction mixture is then cooled and carefully added dropwise to ice-cold saturated aqueous NaHCO$_3$ solution with vigorous stirring. Upon complete quench (pH of the mixture ~8), the layers are separated and the aqueous layer further extracted with CH$_2$Cl$_2$. The combined organic extracts are concentrated in vacuo and the residue taken up in MeOH (20 mL), made alkaline (pH 10) by addition of 10 N aqueous NaOH and treated with ethylenediamine (0.14 mL, 2.0 mmol). After stirring for 30 min, the solvent is removed in vacuo and the residue taken up in EtOAc. Acetic acid is added dropwise to adjust the mixture to pH ~6, and the mixture is then washed with brine. The aqueous layer is further extracted with EtOAc and the combined organic extracts are then dried (Na$_2$SO$_4$), filtered and concentrated in vacuo. The residue is purified by silica gel flash chromatography (gradient elution with 0-10% MeOH in CH$_2$Cl$_2$) to afford the title compound.

Step C: 6-Amino-1,1-difluoro-1,3-dihydrospiro[indene-2,3'-pyrrolo[2,3-b]pyridin]-2'(1'H)-one A mixture of 1,1-difluoro-6-nitro-1,3-dihydrospiro[indene-2,3'-pyrrolo[2,3-b]pyridin]-2'(174)-one (320 mg, 1.0 mmol) and 10% palladium on carbon (20 mg) in MeOH (5 mL) is stirred under an atmosphere of hydrogen for 18 h. The mixture is filtered through a pad of Celite® and the filtrate concentrated in vacuo to give the title compound.

Step D: 1,1-Difluoro-6-iodo-1,3-dihydrospiro[indene-2,3'-pyrrolo[2,3-b]pyridin]-2'(1'H)-one A solution of sodium nitrite (52 mg, 0.75 mmol) in water (2 mL) is added dropwise to a solution of 6-amino-1,1-difluoro-1,3-dihydrospiro[indene-2,3'-pyrrolo[2,3-b]pyridin]-2'(174)-one (106 mg, 0.37 mmol) and p-toluenesulfonic acid (214 mg, 1.12 mmol) in acetonitrile (5 mL) at ambient temperature. After stirring for 30 min, a solution of potassium iodide (155 g, 0.94 mmol) in water (1 mL) is added. The resulting mixture is stirred at ambient temperature for 40 min, then diluted with water (10 mL) and basified by the addition of solid NaOH (47 mg, 1.18 mmol) with stirring. Iodine by-product is reduced by the addition of 10% aqueous sodium thiosulfate solution and stirring for an additional 30 min. The solids are collected by filtration, washed with water, and dried under nitrogen atmosphere to give the title compound.

Step F: Methyl 1,1-difluoro-2'-oxo-1,1',2',3-tetrahydrospiro[indene-2,3'-pyrrolo[2,3-b]pyridine]-6-carboxylate A solution of 1,1-difluoro-6-iodo-1,3-dihydrospiro[indene-2,3'-pyrrolo[2,3-b]pyridin]-2'(174)-one (120 mg, 0.30 mmol), sodium acetate (49 mg, 0.60 mmol) and dichloro 1,1'-bis(diphenylphosphino)ferrocene palladium(II) dichloromethane adduct (6 mg, 0.007 mmol) in MeOH (5 mL) is pressurized to 120 psi with carbon monoxide and then heated at 80° C. for 12 h with stirring. The reaction mixture is diluted with water (20 mL), and the precipitate collected by filtration, washed with water, and dried under nitrogen atmosphere to give the title compound.

Step G: 1,1-Difluoro-2'-oxo-1,1',2',3-tetrahydrospiro[indene-2,3'-pyrrolo[2,3-b]pyridine]-6-carboxylic acid A mixture of methyl 1,1-difluoro-2'-oxo-1,1',2',3-tetrahydrospiro[indene-2,3'-pyrrolo[2,3-b]pyridine]-6-carboxylate (100 mg, 0.30 mmol) and aqueous 6 N sodium hydroxide solution (0.15 mL, 0.91 mmol) in MeOH (5 mL) is heated at reflux for 1 h. The mixture is allowed to cool to ambient temperature before it is acidified to pH ~6 with aqueous 1 N hydrochloric acid solution. The resulting mixture is filtered, and the filtrate is concentrated. The residue is partitioned between water (10 mL) and 2-methyltetrahydrofuran (2-MeTHF, 10 mL). The aqueous layer is extracted with 2-MeTHF (5×10 mL), and the combined organic layers are dried over sodium sulfate and concentrated in vacuo to provide the title compound.

Intermediates 4A & 4B

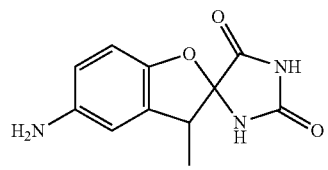

Intermediate 4A

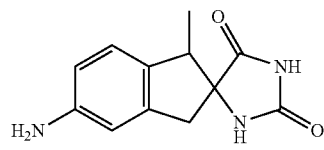

Intermediate 4B

6'-Amino-1'-methyl-1',3'-dihydro-2H,5H-spiro[imidazolidine-4,2'-indene]-2,5-dione (Intermediate 4A) and 5'-Amino-1'-methyl-1',3'-dihydro-2H,5H-spiro[imidazolidine-4,2'-indene]-2,5-dione (Intermediate 4B)

Step A. 1-(1H-Inden-2-yl)pyrrolidine

A mixture of 2-indanone (2.0 g, 15.1 mmol) and pyrrolidine (1.6 mL, 19.7 mmol) in anhydrous toluene (61 mL) was refluxed under nitrogen with azeotropic removal of water (Dean-Stark apparatus) for 2 h. The mixture was then cooled and concentrated to dryness in vacuo to give the title compound. MS:m/z=186.2 (M+1).

Step B. 1-Methyl-1,3-dihydro-2H-inden-2-one

A solution of 1-(1H-inden-2-yl)pyrrolidine (1.00 g, 5.40 mmol) in anhydrous 2-methyltetrahydrofuran (13.3 mL) was cooled to −55° C. and treated with a solution of n-BuLi (1.6 M in hexanes, 4.0 mL, 6.4 mmol) dropwise. The mixture was then stirred at −55° C. for 15 min. Iodomethane (0.4 mL, 6.3 mmol) was added and, after stirring for 5 min, the mixture was quenched by addition of 1 N HCl (6.7 mL). The solvent was removed in vacuo, water (17 mL) was added and the mixture was heated at reflux for 10 min. The mixture was then cooled to ambient temperature and extracted with diethyl ether. The organic layer was washed with brine, and the combined aqueous layers were saturated with NaCl and extracted twice more with diethyl ether. The combined organic extracts were dried (Na$_2$SO$_4$), filtered and concentrated to give an oil, which was treated with TFA (2.5 mL) in CH$_2$Cl$_2$ (2.5 mL) for 5 min. The mixture was concentrated in vacuo and the residue purified by reverse phase preparative HPLC eluting with a gradient of 90:10 to 0:100 A:B where A=0.1% TFA in H$_2$O and B=0.1% TFA in CH$_3$CN). The fractions containing product were combined and concentrated to give an aqueous residue which was saturated with NaCl and extracted with EtOAc (3×). The combined organic extracts were dried (Na$_2$SO$_4$), filtered and concentrated in vacuo to give the title compound. MS: m/z=147.1 (M+1).

Step C. 1'-Methyl-1',3'-dihydro-2H,5H-spiro[imidazolidine-4,2'-indene]-2,5-dione A mixture of 1-methyl-1,3-dihydro-2H-inden-2-one prepared as described above (260 mg, 1.78 mmol), sodium cyanide (261 mg, 5.34 mmol) and ammonium carbonate (1.71 g, 17.8 mmol) in ethanol (4.5 mL) and water (4.5 mL) was heated at 70° C. for 3 h. The mixture was cooled to ambient temperature, diluted with water and the solids removed by filtration. The filtrate was saturated with NaCl and extracted with EtOAc. The saturation-extraction cycle was repeated twice more, and the combined organic extracts were then dried (Na$_2$SO$_4$), filtered and concentrated. The residue was purified by reversed phase preparative HPLC (C18 column) eluting with a gradient of 95:5 to 10:90 A:B where A=0.1% TFA in H$_2$O and B=0.1% TFA in CH$_3$CN) afforded separation of the material into two peaks with identical mass: earlier eluting peak (RT=1.37 min on a 5 min LCMS gradient) showed MS: m/z 217.1 (M+1); later eluting peak (RT=1.43 min on a 5 min LCMS gradient) showed MS: m/z 217.1 (M+1). Concentration of the two product peaks under reduced pressure afforded two pairs of isomers of the title compound as solids.

Step D. 1'-Methyl-6'-nitro-1',3'-dihydro-2H,5H-spiro[imidazolidine-4,2'-indene]-2,5-dione and 1'-Methyl-5'-nitro-1',3'-dihydro-2H,5H-spiro[imidazolidine-4,2'-indene]-2,5-dione The earlier eluting pair of isomers of 1'-methyl-1',3'-dihydro-2H,5H-spiro[imidazolidine-4,2'-indene]-2,5-dione (21 mg, 0.1 mmol) was dissolved in concentrated nitric acid (1 mL) and the solution stirred at ambient temperature for 1 h. The mixture was then poured over crushed ice and extracted with EtOAc. The aqueous layer was saturated with NaCl and extracted again with EtOAc, and the combined organic extracts were then dried (Na2SO4), filtered and concentrated to give the title compounds as a mixture of regio- and stereoisomers. MS: m/z=262.1 (M+1). The later eluting pair of isomers of 1'-methyl-1',3'-dihydro-2H,5H-spiro[imidazolidine-4,2'-indene]-2,5-dione (46 mg, 0.21 mmol) was similarly treated with concentrated nitric acid (1 mL) and converted to the second set of isomers of the title compounds. MS: m/z=262.1 (M+1).

Step E. 6'-Amino-1'-methyl-1',3'-dihydro-2H,5H-spiro[imidazolidine-4,2'-indene]-2,5-dione and 5'-Amino-1'-methyl-1',3'-dihydro-2H,5H-spiro[imidazolidine-4,2'-indene]-2,5-dione The first mixture of isomers of 1'-methyl-6'-nitro-1',3'-dihydro-2H,5H-spiro[imidazolidine-4,2'-indene]-2,5-dione and 1'-methyl-5'-nitro-1',3'-dihydro-2H,5H-spiro[imidazolidine-4,2'-indene]-2,5-dione (27 mg, 0.10 mmol) was dissolved in 1:1 EtOAc:MeOH (3 mL) and 1 M aq. HCl (0.21 mL). 10% Palladium on carbon (6 mg) was added and the mixture stirred under hydrogen atmosphere (balloon) at ambient temperature for 1 h. The mixture was then filtered through Celite®, washing the filter cake well with MeOH, and the filtrate concentrated in vacuo to afford a mixture of the title compounds as hydrochloride salts. MS: m/z=232.2 (M+1). The second set of isomers of 1'-methyl-6'-nitro-1',3'-dihydro-2H,5H-spiro[imidazolidine-4,2'-indene]-2,5-dione and 1'-methyl-5'-nitro-1',3'-dihydro-2H,5H-spiro[imidazolidine-4,2'-indene]-2,5-dione (75 mg, 0.29 mmol) was subjected to similar hydrogenation conditions to afford the remaining isomers of the title compounds as hydrochloride salts. MS: m/z=232.1 (M+1).

Intermediate 5

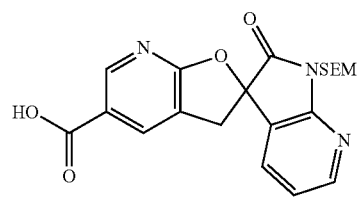 [SMILES: C[Si](C)(C)CCOCN1C(=O)C2(Cc3cc(C(=O)O)cnc3O2)c2cccnc21]

2'-Oxo-1'-((2-(trimethylsilyl)ethoxy)methyl)-1',2'-dihydro-3H-spiro[furo[2,3-b]pyridine-2,3'-pyrrolo[2,3-b]pyridine]-5-carboxylic acid Step A: 5-Formyl-N,N-dimethylfuro[2,3-b]pyridine-2-carboxamide A solution of sodium methoxide in methanol (30% w/w, 38 mL, 0.21 mol) was added to a mixture of methyl 5-aminofuran-2-carboxylate (15 g, 0.11 mol) and 2-[(dimethylamino)methylene]-1,3-bis(dimethyliminio)propane bis(tetrafluoroborate)salt (38 g, 0.11 mol) in an oven-dried sealed tube. The resulting mixture was heated at reflux for 1 h, then cooled to 23° C., and diluted carefully with water. The reaction mixture was concentrated and extracted with ethyl acetate. The organic layer was washed with brine, dried over sodium sulfate, and concentrated. The residue was purified by flash chromatography on silica gel, eluting with 40% ethyl acetate in petroleum ether to give the title compound. $^1$H NMR (300 MHz, CDCl$_3$): δ 8.50 (d, 1H, J=2.0 Hz), 8.13 (d, 1H, J=2.0 Hz), 7.40 (s, 1H), 5.58 (s, 1H), 3.43 (s, 3H), 3.13 (s, 3H).

Step B: 5-(Hydroxymethyl)-N,N-dimethylfuro[2,3-b]pyridine-2-carboxamide

Sodium borohydride (6.0 g, 0.16 mol) was added to a solution of 5-formyl-N,N-dimethylfuro[2,3-b]pyridine-2-carboxamide (6.9 g, 0.032 mol) in methanol (80 mL) and THF (20 mL) at 0° C., and the resulting mixture was gradually warmed to 23° C. and stirred for 1 h. The excess of sodium borohydride was carefully quenched with water. The reaction mixture was concentrated, and then extracted with ethyl acetate. The organic layer was washed with brine, dried over sodium sulfate, and concentrated. The residue was purified by flash chromatography on silica gel eluting with 70% ethyl acetate in petroleum ether to give the title compound. MS: m/z=221.0 (M+1).

Step C: 5-(((4-Methoxybenzyl)-oxy)-methyl)-N,N-dimethylfuro[2,3-b]pyridine-2-carboxamide An ice-cold solution of 5-(hydroxymethyl)-N,N-dimethylfuro[2,3-b]pyridine-2-carboxamide (4.2 g, 0.019 mol) in DMF (15 mL) was added dropwise to a suspension of sodium hydride (60% dispersion in mineral oil, 1.14 g, 0.0286 mol) in DMF (15 mL) at 0° C. After the resulting mixture was stirred at 0° C. for 15 min, 4-methoxybenzyl chloride (3.89 g, 286 mmol) was added. The reaction mixture was gradually warmed to 23° C., and stirred for 1 h. The excess of sodium hydride was carefully quenched with water (15 mL). The reaction mixture was extracted with ethyl acetate. The organic layer was washed with brine, dried over sodium sulfate, and concentrated. The residue was purified by flash chromatography on silcia gel eluting with 35% ethyl acetate in petroleum ether to give the title compound. MS: m/z=341.2 (M+1).

Step D: 5-(((4-Methoxybenzyl)-oxy)methyl)furo[2,3-b]pyridine-2-carboxylic acid In a sealed tube, a mixture of a solution of 5-(((4-methoxybenzyl)-oxy)-methyl)-N,N-dimethylfuro[2,3-b]pyridine-2-carboxamide (2.4 g, 7.1 mmol) in methanol (28 mL) and a solution of potassium hydroxide (0.79 g, 14 mmol) in water (7 mL) was heated at reflux for 1 h. After cooling to ambient temperature, the reaction mixture was partitioned between saturated aqueous citric acid solution and ethyl acetate. The organic layer was dried over sodium sulfate, and concentrated to give the title compound. MS: m/z=314.2 (M+1).

Step E: N-(3-Bromopyridin-2-yl)-5-(((4-methoxybenzyl)oxy)methyl)furo[2,3-b]pyridine-2-carboxamide In an oven-dried sealed tube, a mixture of 5-(((4-methoxybenzyl)-oxy)methyl)furo[2,3-b]pyridine-2-carboxylic acid (2.0 g, 6.4 mmol), 3-bromo-2-amino pyridine (3.31 g, 19.2 mmol), N-methyl morpholine (1.93 g, 19.2 mmol) and N,N,N',N'-tetramethylchloroformamidinium hexafluorophosphate (3.58 g, 12.8 mmol) in DMF (20 mL) was heated to 70° C. for 5 h. The reaction mixture was partitioned between saturated aqueous sodium bicarbonate solution and ethyl acetate. The organic layer was washed with water, brine, dried over sodium sulfate, and concentrated. The residue was purified by flash chromatography on silica gel eluting with 40% ethyl acetate in petroleum ether to give the title compound. MS: m/z=468.5 (M+1).

Step F: N-(3-Bromopyridin-2-yl)-5-(((4-methoxybenzyl)oxy)methyl)-N-((2-(trimethylsilyl)ethoxy)methyl)furo[2,3-b]pyridine-2-carboxamide 2-Trimethylsilylethoxymethyl chloride (0.13 g, 0.81 mmol) was added to a solution of N-(3-bromopyridin-2-yl)-5-(((4-methoxybenzyl)oxy)methyl)furo[2,3-b]pyridine-2-carboxamide (0.29 g, 0.62 mmol) and cesium carbonate (0.61 g, 1.8 mmol) in DMF (6.2 mL) at 0° C. The reaction mixture was gradually warmed to 23° C. and stirred for 2 h, then partitioned between saturated aqueous sodium bicarbonate solution and ethyl acetate. The organic layer was dried over sodium sulfate, and concentrated. The residue was purified by flash chromatography on silica gel eluting with 18% ethyl acetate in petroleum ether to give the title compound. MS: m/z=600.2 (M+1).

Step G: 5-(((4-Methoxybenzyl)oxy)methyl)-1'-((2-(trimethylsilyl)ethoxy)methyl)-3H-spiro[furo[2,3-b]pyridine-2,3'-pyrrolo[2,3-b]pyridin]-2'(1'H)-one A deoxygenated solution of tributyltin hydride (0.779 g, 2.68 mmol) and AIBN (43 mg, 0.26 mmol) in benzene (44 mL) was added dropwise over 2 h to a deoxygenated solution of N-(3-bromopyridin-2-yl)-5-(((4-methoxybenzyl)oxy)methyl)-N-((2-(trimethylsilyl)ethoxy)methyl)furo[2,3-b]pyridine-2-carboxamide (0.80 g, 1.3 mmol) and AIBN (87 mg, 0.53 mmol) in benzene (86 mL) at reflux, and the heating was continued for 1 h. The excess tributyl tinhydride was quenched with thiophenol (0.5 mL) and the reaction mixture was concentrated. The residue was purified by flash chromatography on silica gel eluting with 20% ethyl acetate in petroleum ether to give the title compound as a racemic mixture. MS: m/z=520.2 (M+1).

Step H: 5-(Hydroxymethyl)-1'-((2-(trimethylsilyl)ethoxy)methyl)-3H-spiro[furo[2,3-b]pyridine-2,3'-pyrrolo[2,3-b]pyridin]-2'(1'H)-one DDQ (0.533 g, 2.35 mmol) was added to a solution of 5-(((4-methoxybenzyl)oxy)methyl)-1'-((2-(trimethylsilyl)ethoxy)methyl)-3H-spiro[furo[2,3-b]pyridine-2,3'-pyrrolo[2,3-b]pyridin]-2'(1'H)-one (0.61 g, 1.2 mmol) in dichloromethane (16 mL) and water (4 mL) at 0° C. The resulting mixture was gradually warmed to 23° C. and stirred for 1 h, then partitioned between saturated aqueous sodium bicarbonate solution and dichloromethane. The organic layer was dried over sodium sulfate, and concentrated. The residue was purified by flash chromatography on silica gel eluting with 50% ethyl acetate in petroleum ether to give the title compound as a racemic mixture. MS: m/z=400.2 (M+1).

Step I: 2'-Oxo-1'-((2-(trimethylsilyl)ethoxy)methyl)-1',2'-dihydro-3H-spiro[furo[2,3-b]pyridine-2,3'-pyrrolo[2,3-b]pyridine]-5-carboxylic acid Freshly prepared Jones reagent was added drop wise to a solution of 5-(hydroxymethyl)-1'-((2-(trimethylsilyl)ethoxy)methyl)-3H-spiro[furo[2,3-b]pyridine-2,3'-pyrrolo[2,3-b]pyridin]-2'(1'H)-one (0.24 g, 0.60 mmol) in acetone (10 mL) at 0° C. until the starting material was completely consumed. The acidic mixture was neutralized carefully with saturated aqueous sodium bicarbonate solution and acidified with saturated aqueous citric acid solution to pH 5-6, then extracted with ethyl acetate (5×). The combined organic layers were dried over sodium sulfate, and concentrated. The residue was purified by flash chromatography on silica gel eluting with 5% methanol in dichloromethane to give the title compound as a racemic mixture. MS: m/z=414.2 (M+1); ¹H NMR (300 MHz, CD₃OD): δ 8.70 (d, 1H, J=1.8 Hz), 8.34 (dd, 1H, J=1.5, 5.3 Hz), 8.29 (d, 1H, J=1.8 Hz), 7.89 (dd, 1H, J=1.5, 7.4 Hz), 7.19 (dd, 1H, J=5.3, 7.4 Hz), 5.26 (s, 2H), 3.78-3.65 (m, 4H), 0.95 (t, 2H, J=8 Hz), 0.005 (s, 9H).

Intermediates 6A & 6B

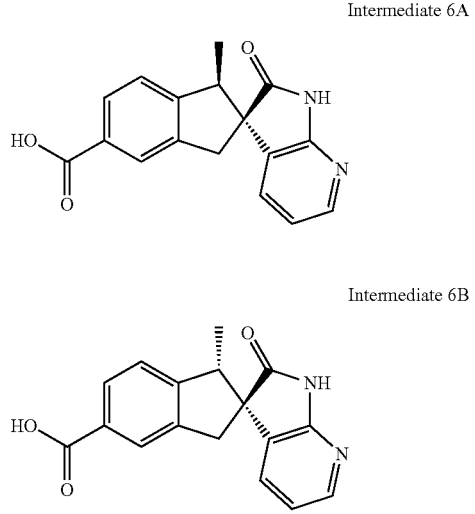

Intermediate 6A

Intermediate 6B (1R,2S and 1S, 2R)-1-Methyl-2'-oxo-1,1',2',3-tetrahydrospiro[indene-2,3'-pyrrolo[2,3-b]pyridine]-5-carboxylic acid (Intermediate 6A) and (1R,2R and 1S, 2S)-1-methyl-2'-oxo-1,1',2',3-tetrahydrospiro[indene-2,3'-pyrrolo[2,3-b]pyridine]-5-carboxylic acid (Intermediate 6B)

Step A. Methyl 4-(1-bromoethyl)benzoate

A solution of trimethylsillyldiazomethane in THF (2M, 49.1 mL, 98.3 mmol) was added dropwise to a solution of 4-(1-bromoethyl)benzoic acid (15 g, 66 mmol) in methanol (75 mL) and THF (75 mL) at 0° C. The resulting mixture was stirred at 23° C. for 3 h, then concentrated and partitioned between ethyl acetate and saturated aqueous sodium bicarbonate solution (2×). The combined organic layers were washed with water and brine, dried over anhydrous sodium sulfate, and concentrated to give the title compound. ¹H NMR (400 MHz, CDCl₃): δ 8.02 (d, 2H, J=8.5 Hz), 7.51 (d, 2H, J=8.2 Hz), 5.21 (q, 1H, J=6.7 Hz), 3.92 (s, 3H), 2.06 (d, 3H, J=7.0 Hz).

Step B. Methyl 4-(4-(tert-butoxy)-3-(diethoxyphosphoryl)-4-oxobutan-2-yl)benzoate Sodium hydride (60% dispersion in mineral oil, 2.98 g, 74.7 mmol) was added portionwise to a solution of tert-butyl 2-(diethoxyphosphoryl)acetate (12.6 g, 49.8 mmol) in anhydrous DMF (150 mL) at 23° C. over 20 min. The reaction mixture was cooled to 0° C., and then a solution of methyl 4-(1-bromoethyl)benzoate (12.1 g, 49.8 mmol) in anhydrous DMF (100 mL) was added dropwise over 15 min. The resulting mixture was stirred at room temperature for 5 h, then concentrated under reduced pressure. The residue was partitioned between ethyl acetate and water (2×). The combined organic layers were washed with brine and dried over anhydrous sodium sulfate, and concentrated. The residue was purified by flash chromatography on silica gel eluting with 25% ethyl acetate in petrolum ethers to give the title compound. MS: m/z=829.4 (2M+1).

Step C. Methyl 4-(3-(tert-butoxycarbonyl)but-3-en-2-yl)benzoate

Potassium carbonate (9.16 g, 66.2 mmol) and paraformaldehyde (2.48 g, 82.7 mmol) were added to a solution of methyl 4-(4-(tert-butoxy)-3-(diethoxyphosphoryl)-4-oxobutan-2-yl)benzoate (13.7 g, 33.1 mmol) in anhydrous THF (250 mL), respectively. The reaction mixture was heated at reflux for 20 h, then cooled, and concentrated. The residue was purified by flash chromatography on silica gel eluting with 5% ethyl acetate in petroleum ether to give the title compound. MS: m/z=235.0 (M−tBu); ¹H NMR (400 MHz, CDCl₃): δ 7.97 (d, 2H, J=8.5 Hz), 7.28 (d, 2H, J=8.5 Hz), 6.26-6.32 (m, 1H), 5.56-5.61 (m, 1H), 4.01 (q, 1H, J=7.1 Hz), 3.92 (s, 3H), 1.42 (d, 3H, J=7.0 Hz), 1.33 (s, 9H).

Step D. 3-(4-(Methoxycarbonyl)phenyl)-2-methylenebutanoic acid

Trifluoroacetic acid (21.7 mL, 283 mmol) was added to a solution of methyl 4-(3-(tert-butoxycarbonyl)but-3-en-2-yl)benzoate (8.7 g, 30 mmol) in anhydrous dichloromethane (85 mL), and the mixture was stirred at 23° C. for 5 h. The solvents were removed under reduced pressure and the residue was triturated with hexane. The solid was collected by filtration and dried under vacuo to give the title compound. MS: m/z=233.0 (M+1).

Step E. 2-Amino-3-bromopyridine 1-oxide mCPBA (12.0 g, 69.3 mmol) was added portionwise over 5 min to a solution of 3-bromopyridin-2-amine (10 g, 58 mmol) in anhydrous acetone (150 mL) at 0° C. The resulting mixture was warmed to 23° C. and stirred for 1 h, then concentrated. The residue was partitioned between a solution of 5% methanol in chloroform and saturated aqueous sodium hydroxide solution (3×). The combined organic layers were washed with brine, dried over anhydrous sodium sulfate, and concentrated to give the title compound. MS: m/z=189.0 (M+1).

Step F. 3-Bromo-2-(3-(4-(methoxycarbonyl)phenyl)-2-methylenebutanamido)pyridine 1-oxide A mixture of 3-(4-(methoxycarbonyl)phenyl)-2-methylenebutanoic acid (1.0 g, 4.2 mmol), HATU (1.9 g, 5.1 mmol), 2-amino-3-bromopyridine 1-oxide (0.88 g, 4.6 mmol) and diisopropyl ethylamine (2.22 mL, 12.5 mmol) in anhydrous DMF (10 mL) was stirred at 23° C. for 1 h, then concentrated. The residue was partitioned between ethyl acetate and brine (2×). The combined organic layers were dried over anhydrous sodium sulfate, and concentrated. The residue was triturated with acetonitrile (20 mL). The solid was filtered and dried under vacuum to give the title compound. MS: m/z=406.0 (M+1).

Step G. 5-(Methoxycarbonyl)-1-methyl-2'-oxo-1,1', 2',3-tetrahydrospiro[indene-2,3'-pyrrolo[2,3-b]pyridine]7'-oxide Bis(triphenylphosphine)palladium(II) dichloride (0.17 g, 0.24 mmol) was added to a deoxygenated mixture of 3-bromo-2-(3-(4-(methoxycarbonyl)phenyl)-2-methylenebutanamido)pyridine 1-oxide (2.0 g, 5.0 mmol), cesium carbonate (4.03 g, 12.4 mmol) in anhydrous DMF (40 mL). The resulting mixture was heated at 110° C. under nitrogen for 20 h, then cooled and filtered through Celite®. The filter cake was washed with ethyl acetate. The filtrate was concentrated, and partitioned between ethyl acetate and brine (2×). The combined organic layers were dried over anhydrous sodium sulfate and concentrated to give the title compound which was used without further purification in next step.

Step H. Methyl (1R,2S and 1S,2R)-1-methyl-2'-oxo-1,1',2',3-tetrahydrospiro[indene-2,3'-pyrrolo[2,3-b]pyridine]-5-carboxylate and methyl (1R,2R and 1S,2S)-1-methyl-2'-oxo-1,1',2',3-tetrahydrospiro[indene-2,3'-pyrrolo[2,3-b]pyridine]-5-carboxylate A mixture of 5-(methoxycarbonyl)-1-methyl-2'-oxo-1,1', 2',3-tetrahydrospiro[indene-2,3'-pyrrolo[2,3-b]pyridine]7'-oxide (1.4 g, 4.3 mmol) and PBr$_3$ (2.02 mL, 21.6 mmol) in anhydrous dichloromethane (20 mL) was stirred for 2 h, then concentrated. The residue obtained was partioned between saturated aqueous sodium bicarbonate solution and ethyl acetate. The organic layer was washed with water, brine, dried over anhydrous sodium sulfate, and concentrated. The residue was purified by reverse phase HPLC (C-18 column), eluting with with 30% acetonitrile in water (0.1% TFA used as a modifier) initially, grading to 100% acetonitrile to give the title compounds as racemic mixtures.

Isomer set A (1$^{st}$ to elute), methyl (1R,2S and 1S,2R)-1-methyl-2'-oxo-1,1',2',3-tetrahydrospiro[indene-2,3'-pyrrolo[2,3-b]pyridine]-5-carboxylate: MS: m/z=309.2 (M+1); $^1$H NMR (400 MHz, CDCl$_3$): δ 8.04-7.98 (m, 3H), 7.55 (d, 1H, J=6.8 Hz), 7.29 (d, 1H, J=8.0 Hz), 7.13 (br s, 1H), 3.94 (s, 3H), 3.94-3.80 (m), 3.63 (d, 1H, J=15.4 Hz), 3.29 (d, 1H, J=15.4 Hz) 1.36 (d, 3H, J=6.6 Hz).

Isomer set B (2$^{nd}$ to elute), methyl (1R,2R and 1S,2S)-1-methyl-2'-oxo-1,1',2',3-tetrahydrospiro[indene-2,3'-pyrrolo[2,3-b]pyridine]-5-carboxylate: MS: m/z=309.2 (M+1); $^1$H NMR (400 MHz, CDCl$_3$): δ δ 8.14-7.95 (m, 3H), 7.25 (d, 1H, J=6.3 Hz), 6.84-6.83 (m, 2H), 3.98-3.93 (m), 3.94 (s, 3H), 3.69 (d, 1H, J=15.4 Hz), 3.06 (d, 1H, J=15.4 Hz) 1.04 (d, 3H, J=7.0 Hz).

Step I. (1R,2S and 1S,2R)-1-Methyl-2'-oxo-1,1',2',3-tetrahydrospiro[indene-2,3'-pyrrolo[2,3-b]pyridine]-5-carboxylic acid, Intermediate 6A A mixture of lithium hydroxide monohydrate (31 mg, 0.73 mmol) and methyl (1R,2S and 1S,2R)-1-methyl-2'-oxo-1,1', 2',3-tetrahydrospiro[indene-2,3'-pyrrolo[2,3-b]pyridine]-5-carboxylate (75 mg, 0.24 mmol) in THF (5 mL) and methanol (5 mL) was stirred at 23° C. for 5 h, concentrated. The residue was acidified with saturated aqueous citric acid solution to pH 2, and extracted with ethyl acetate (2×). The combined organic layers were washed with water, brine, dried over anhydrous sodium sulfate, and concentrated to give the title compound as a racemic mixture. MS: m/z=295.2 (M+1); $^1$H NMR (400 MHz, DMSO-d$_6$): δ 12.75 (br. s, 1H), 10.96 (s, 1H), 8.10 (d, 1H, J=3.9 Hz), 7.76-7.87 (m, 3H), 7.30 (d, 1H, J=7.9 Hz), 7.01 (dd, 1H, J=5.1, 7.3 Hz), 3.75 (q, 1H, J=7.0 Hz), 3.39 (d, 1H, J=16.1 Hz), 3.27 (d, 1H, J=16.1 Hz), 1.11 (d, 3H, J=7.0 Hz).

(1R,2R and 1S,2S)-1-Methyl-2'-oxo-1,1',2',3-tetrahydrospiro[indene-2,3'-pyrrolo[2,3-b]pyridine]-5-carboxylic acid, Intermediate 6B Starting with methyl (1R,2S and 1S,2R)-1-methyl-2'-oxo-1,1',2',3-tetrahydrospiro[indene-2,3'-pyrrolo[2,3-b]pyridine]-5-carboxylate, the procedure described for Intermediate 6A was followed to provide the title compound as a racemic mixture. MS: m/z=295.2 (M+1); $^1$H NMR (400 MHz, CD$_3$OD): δ 7.93-8.10 (m, 3H), 7.35 (d, 1H, J=8.0 Hz), 6.79-6.89 (m, 2H), 3.87 (q, 1H, J=6.8 Hz), 3.60 (d, 1H, J=15.5 Hz), 3.11 (d, 1H, J=15.5 Hz), 1.05 (d, 3H, J=7.0 Hz).

EXAMPLE 1

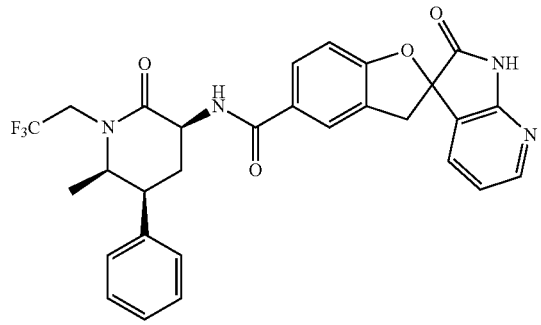 [SMILES: C[C@@H]1[C@H](c2ccccc2)C[C@H](NC(=O)c2ccc3c(c2)CC2(O3)C(=O)Nc3ncccc32)C(=O)N1CC(F)(F)F]

N-[(3S,5S,6R)-6-Methyl-2-oxo-5-phenyl-1-(2,2,2-trifluoroethyl)piperidin-3-yl]-2'-oxo-1',2'-dihydro-3H-spiro[1-benzofuran-2,3'-pyrrolo[2,3-b]pyridine]-5-carboxamide (Benzotriazol-1-yloxy)tris(dimethylamino)phosphonium hexafluorophosphate (90 mg, 0.20 mmol) is added to a solution of 2'-oxo-1',2'-dihydro-3H-spiro[benzofuran-2,3'-pyrrolo[2,3-b]pyridine]-5-carboxylic acid (described in Intermediate 2) (48 mg, 0.17 mmol), (3S,5S,6R)-3-amino-6-methyl-5-phenyl-1-(2,2,2-trifluoroethyl)piperidin-2-one hydrochloride (described in Intermediate 1, 54 mg, 0.17 mmol), and N,N-diisopropylethylamine (0.15 mL, 0.84 mmol) in DMF (3 mL), and the resulting mixture is stirred at ambient temperature for 3 h. The reaction mixture is then partitioned between saturated aqueous sodium bicarbonate solution (20 mL) and ethyl actetate (3×20 mL). The combined organic layers are washed with brine, dried over sodium sulfate, and concentrated in vacuo. The residue is purified by flash column chromatography on silica gel, eluting with a gradient of CH₂Cl₂:MeOH—100:0 to 90:10, to afford the title compound as a mixture of diastereomers.

EXAMPLE 2

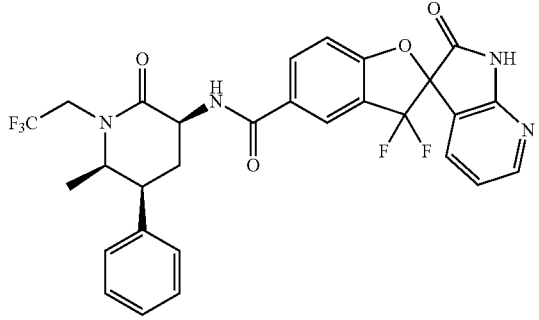 [SMILES: C[C@@H]1[C@H](c2ccccc2)C[C@H](NC(=O)c2ccc3c(c2)C(F)(F)C2(O3)C(=O)Nc3ncccc32)C(=O)N1CC(F)(F)F]

3,3-Difluoro-N-[(3S,5S,6R)-6-methyl-2-oxo-5-phenyl-1-(2,2,2-trifluoroethyl)piperidin-3-yl]-2'-oxo-1,1',2',3-tetrahydrospiro[indene-2,3'-pyrrolo[2,3-b]pyridine]-5-carboxamide (Benzotriazol-1-yloxy)tris(dimethylamino)phosphonium hexafluorophosphate (90 mg, 0.20 mmol) is added to a solution of 1,1-difluoro-2'-oxo-1,1',2',3-tetrahydrospiro[indene-2,3'-pyrrolo[2,3-b]pyridine]-6-carboxylic acid (described in Intermediate 3) (54 mg, 0.17 mmol), (3S,5S,6R)-3-amino-6-methyl-5-phenyl-1-(2,2,2-trifluoroethyl)piperidin-2-one hydrochloride (described in Intermediate 1) (54 mg, 0.17 mmol), and N,N-diisopropylethylamine (0.15 mL, 0.84 mmol) in DMF (3 mL), and the resulting mixture is stirred at ambient temperature for 3 h. The reaction mixture is then partitioned between saturated aqueous sodium bicarbonate solution (20 mL) and ethyl actetate (3×20 mL). The combined organic layers are washed with brine, dried over sodium sulfate, and concentrated in vacuo. The residue is purified by flash column chromatography on silica gel, eluting with a gradient of CH₂Cl₂:MeOH—100:0 to 90:10, to afford the title compound as a mixture of diastereomers.

EXAMPLE 3

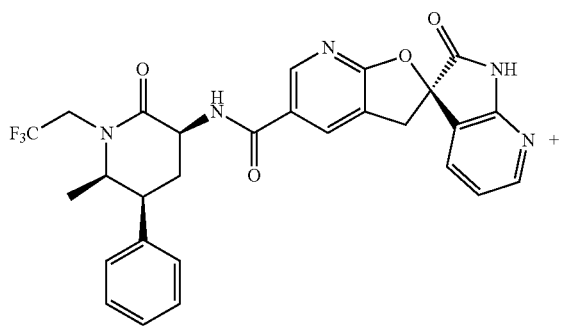

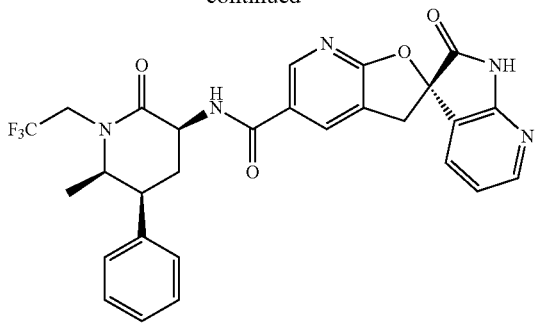

(R)—N-((3S,5S,6R)-6-Methyl-2-oxo-5-phenyl-1-(2,2,2-trifluoroethyl)piperidin-3-yl)-2'-oxo-1',2'-dihydro-3H-spiro[furo[2,3-b]pyridine-2,3'-pyrrolo[2,3-b]pyridine]-5-carboxamide and (S)-N-((3S,5S,6R)-6-Methyl-2-oxo-5-phenyl-1-(2,2,2-trifluoroethyl)piperidin-3-yl)-2'-oxo-1',2'-dihydro-3H-spiro[furo[2,3-b]pyridine-2,3'-pyrrolo[2,3-b]pyridine]-5-carboxamide Step A: (R and S)—N-((3S,5S,6R)-6-Methyl-2-oxo-5-phenyl-1-(2,2,2-trifluoroethyl)piperidin-3-yl)-2'-oxo-1'-((2-(trimethylsilyl)ethoxy)methyl)-1',2'-dihydro-3H-spiro[furo[2,3-b]pyridine-2,3'-pyrrolo[2,3-b]pyridine]-5-carboxamide A mixture of 2'-oxo-1'-((2-(trimethylsilyl)ethoxy)methyl)-1',2'-dihydro-3H-spiro[furo[2,3-b]pyridine-2,3'-pyrrolo[2,3-b]pyridine]-5-carboxylic acid, (described in Intermediate 5) (0.095 g, 0.23 mmol), (3S,5S,6R)-3-amino-6-methyl-5-phenyl-1-(2,2,2-trifluoroethyl)piperidin-2-one, (described in Intermediate 1) (0.098 g, 0.35 mmol), N,N-diisopropylethylamine (0.12 mL, 0.69 mmol), 1-ethyl-3-(3-dimethylaminopropyl) carbodiimide hydrochloride (0.065 g, 0.35 mmol) and HOBT (0.015 g, 0.12 mmol) in DMF (3 mL) was stirred initially at 0° C. for 15 min, then gradually warmed to 23° C. and stirred for 3 h. The reaction mixture was partitioned between saturated aqueous sodium bicarbonate solution and ethyl acetate. The organic layer was dried over sodium sulfate, and concentrated. The residue was purified by flash chromatography on silica gel eluting with 50% ethyl acetate in petroleum ether to give the title compounds as a 1:1 mixture of isomers. MS: m/z=682.5 (M+1).

Step B: (R)—N-((3S,5S,6R)-6-Methyl-2-oxo-5-phenyl-1-(2,2,2-trifluoroethyl)piperidin-3-yl)-2'-oxo-1',2'-dihydro-3H-spiro[furo[2,3-b]pyridine-2,3'-pyrrolo[2,3-b]pyridine]-5-carboxamide and (S)—N-((3S,5S,6R)-6-methyl-2-oxo-5-phenyl-1-(2,2,2-trifluoroethyl)piperidin-3-yl)-2'-oxo-1',2'-dihydro-3H-spiro[furo[2,3-b]pyridine-2,3'-pyrrolo[2,3-b]pyridine]-5-carboxamide A solution of stannous tetrachloride in dichloromethane (1 M, 0.19 mL, 0.19 mmol) was added to a solution of (R and S)—N-((3S,5S,6R)-6-methyl-2-oxo-5-phenyl-1-(2,2,2-trifluoroethyl)piperidin-3-yl)-2'-oxo-1'-((2-(trimethylsilyl)ethoxy)methyl)-1',2'-dihydro-3H-spiro[furo[2,3-b]pyridine-2,3'-pyrrolo[2,3-b]pyridine]-5-carboxamide (0.085 g, 0.12 mmol) in dichloromethane (3 mL) at 0° C. The reaction mixture was stirred for 1 h, then partitioned between saturated aqueous sodium bicarbonate solution and ethyl acetate. The organic layer was dried over sodium sulfate, and concentrated. The residue was purified by flash chromatography on silica gel eluting with 90% ethyl acetate in petroleum ether to give a 1:1 mixture of isomers which were separated by chiral SFC (Whelco R,R column), eluting with 65% CO$_2$ in methanol using 0.1% diethylamine as modifier to provide the title compounds.

Isomer A (1$^{st}$ to elute): MS: m/z=538.2 (M+1); $^1$H NMR (400 MHz, CDCl$_3$) δ 8.55 (s, 1H), 8.25 (d, 1H, J=5.7 Hz), 8.10 (s, 1H), 7.72 (d, 1H, J=7.4 Hz), 7.36 (t, 2H, J=7.4 Hz), 7.29 (d, 1H, J=7.3 Hz), 7.22 (d, 2H, J=7.6 Hz), 7.04 (dd, 1H, J=7.5, 5.3 Hz), 4.95 (dd, 1H, J=15.4, 8.8 Hz), 4.23-4.29 (m, 1H), 3.90 (t, 1H, J=6.2 Hz), 3.77 (d, 1H, J=16.9 Hz), 3.59 (d, 1H, J=13.2 Hz), 3.51 (d, 1H, J=16.9 Hz), 3.33 (dd, 1H, J=15.3, 8.1 Hz), 2.92-2.94 (m, 2H), 2.54 (s, 1H), 1.13 (d, 3H, J=6.5 Hz).

Isomer B (2$^{nd}$ to elute): MS: m/z=538.2 (M+1); $^1$H NMR (400 MHz, CDCl$_3$) δ 8.63 (s, 1H), 8.26 (d, 1H, J=5.3 Hz), 8.03 (s, 1H); 7.76 (d, 1H, J=7.5 Hz), 7.71 (s, 1H), 7.37 (t, 2H, J=7.5 Hz), 7.29 (t, 1H, J=7.3 Hz), 7.22 (d, 2H, J=7.6 Hz), 7.05 (dd, 1H, J=7.4, 5.3 Hz), 4.93-4.95 (m, 1H), 4.34-4.40 (m, 1H), 3.92 (t, 1H, J=6.0 Hz), 3.71 (s, 1H), 3.62 (d, 1H, J=11.6 Hz), 3.46 (d, 1H, J=16.9 Hz), 3.29-3.31 (m, 1H), 2.70-2.72 (m, 2H), 1.09 (d, 3H, J=6.5 Hz).

EXAMPLES 4A & 4B

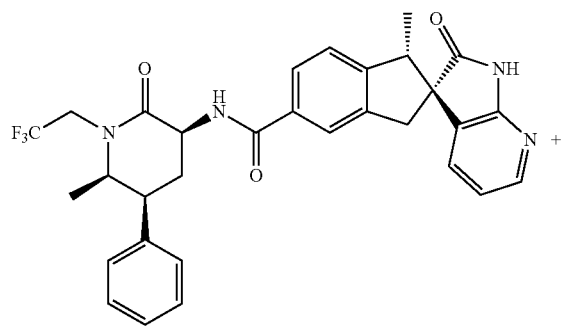

4A

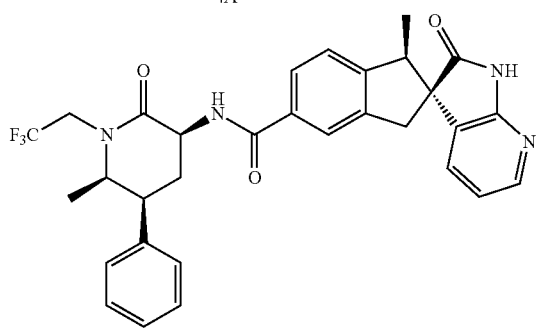

4B (1S,2R)-1-Methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide (Example 4A) and (1R,2S)-1-methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide (Example 4B)

A mixture of (1R,2S and 1S,2R)-1-methyl-2'-oxo-1,1',2',3-tetrahydrospiro[indene-2,3'-pyrrolo[2,3-b]pyridine]-5-carboxylic acid, (described in Intermediate 6A) (65 mg, 0.22 mmol), (3S,5S,6R)-3-amino-6-methyl-5-phenyl-1-(2,2,2-trifluoroethyl) piperidin-2-one, (described in Intermediate 1) (63 mg, 0.22 mmol), 1-ethyl-3-(3-dimethylaminopropyl)carbodiimide hydrochloride (63 mg, 0.33 mmol), HOBT (15 mg, 0.11 mmol) and N,N-diisopropylethylamine (0.12 mL, 0.66 mmol) in anhydrous DMF (15 mL) was stirred at 23° C. for 5.5 h, and then concentrated. The residue was partitioned between ethyl acetate and saturated aqueous sodium bicarbonate solution. The organic layer was washed with water and brine, dried over anhydrous sodium sulfate, and concentrated. The residue was purified by reverse-phase HPLC (C-18 column) eluting with 30% acetonitrile in water (0.1% TFA used as a modifier) initially, grading to 100% acetonitrile to give the title compounds as a 1:1 mixture of isomers, which were separated by ChiralPak AS, eluting with 75% CO$_2$ in methanol using 0.1% diethylamine as modifier.

Isomer A 1 (1$^{st}$ peak to elute), (1S,2R)-1-methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide (Example 4A): MS: m/z=563.2 (M+1); $^1$HNMR (500 MHz, CDCl$_3$) δ 8.16 (d, 1H, J=5.3 Hz), 7.76-7.78 (m, 2H), 7.29-7.31 (m, 7H), 6.92 (dd, 1H, J=7.3, 5.3 Hz), 4.94-4.96 (m, 1H); 4.52 (dt, 1H, J=11.6, 6.0 Hz), 3.92 (t, 1H, J=6.2 Hz), 3.61-3.64 (m, 2H), 3.26-3.28 (m, 2H), 2.75 (d, 2H, J=13.3 Hz), 2.58 (q, 1H, J=12.5 Hz), 1.31 (d, 3H, J=7.1 Hz), 1.06 (d, 3H, J=6.5 Hz).

Isomer B (2$^{nd}$ peak to elute), (1R,2S)-1-methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide (Example 4B): MS: m/z=563.2 (M+1); $^1$HNMR (500 MHz, CDCl$_3$) δ 8.15 (d, 1H, J=5.3 Hz), 7.75 (d, 2H, J=4.4 Hz), 7.36 (t, 3H, J=7.8 Hz), 7.24-7.25 (m, 4H), 6.92 (dd, 1H, J=7.4, 5.3 Hz), 4.94-4.96 (m, 1H), 4.49 (dt, 1H, J=11.6, 6.0 Hz), 3.92 (t, 1H, J=6.2 Hz), 3.60-3.63 (m, 2H), 3.26-3.28 (m, 2H), 2.73 (d, 2H, J=7.8 Hz), 2.60 (q, 1H, J=12.5 Hz), 1.31 (d, 3H, J=7.1 Hz), 1.07 (d, 3H, J=6.5 Hz).

EXAMPLES 5A & 5B

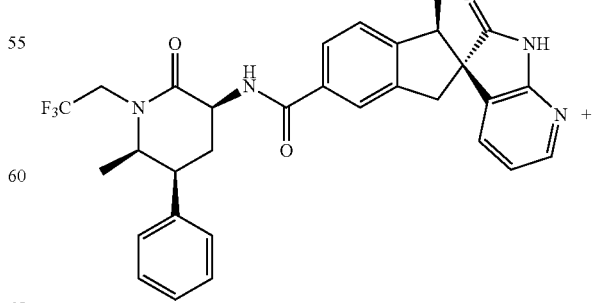

5A

-continued

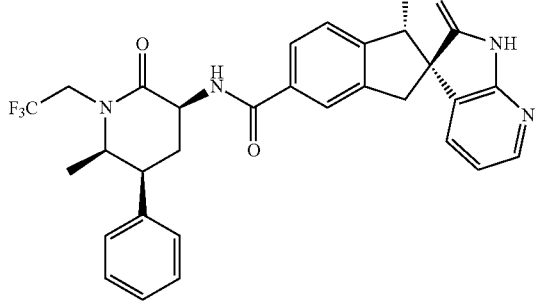

5B (1R,2R)-1-Methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide (Example 5A) and (1S,2S)-1-methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide (Example 5B)

A mixture of (1R,2R and 1S,2S)-1-methyl-2'-oxo-1,1',2',3-tetrahydrospiro[indene-2,3'-pyrrolo[2,3-b]pyridine]-5-carboxylic acid, (described in Intermediate 6B) (80 mg, 0.27 mmol), (3S,5S,6R)-3-amino-6-methyl-5-phenyl-1-(2,2,2-trifluoroethyl)piperidin-2-one, (described in Intermediate 1) (77 mg, 0.27 mmol), 1-ethyl-3-(3-dimethylaminopropyl)carbodiimide hydrochloride (78 mg, 0.41 mmol), HOBT (18 mg, 0.14 mmol) and N,N-diisopropylethylamine (0.14 mL, 0.82 mmol) in anhydrous DMF (20 mL) was stirred at 23° C. for 5.5 h, and then concentrated under reduced pressure. The residue was partitioned between ethyl acetate and saturated aqueous sodium bicarbonate solution. The organic layer was washed with water and brine, dried over anhydrous sodium sulfate, and concentrated. The residue was purified by reverse-phase HPLC (C-18 column) eluting with 30% acetonitrile in water (0.1% TFA used as a modifier) initially, grading to 100% acetonitrile to give the title compounds as a 1:1 mixture of isomers, which were separated by ChiralPak AS, eluting with 75% $CO_2$ in methanol using 0.1% diethylamine as modifier.

Isomer A (1$^{st}$ peak to elute), (1R,2R)-1-methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide (Example 5A): MS: m/z=563.2 (M+1); $^1$HNMR (500 MHz, CDCl$_3$) δ 8.14 (d, 1H, J=5.1 Hz), 7.76-7.78 (m, 2H), 7.48 (d, 1H, J=5.5 Hz), 7.36 (t, 2H, J=7.5 Hz), 7.22 (d, 3H, J=7.5 Hz), 6.73-6.74 (m, 2H), 4.94-4.96 (m, 1H), 4.49 (dt, 1H, J=11.5, 6.0 Hz), 3.88-3.95 (m, 2H), 3.65 (t, 2H, J=14.6 Hz), 3.28-3.30 (m, 1H), 2.83 (d, 1H, J=8.0 Hz), 2.75 (t, 1H, J=8.5 Hz), 2.64 (q, 1H, J=12.4 Hz), 1.08 (d, 3H, J=6.5 Hz), 1.03 (d, 3H, J=7.1 Hz).

Isomer B (2$^{nd}$ peak to elute), (1S,2S)-1-methyl-N-((3S,5S,6R)-6-methyl-2-oxo-5-phenyl-1-(2,2,2-trifluoroethyl)piperidin-3-yl)-2'-oxo-1,1',2',3-tetrahydrospiro[indene-2,3'-pyrrolo[2,3-b]pyridine]-5-carboxamide (Example 5B): MS: m/z=563.2 (M+1); $^1$HNMR (500 MHz, CDCl$_3$) δ 8.14 (d, 1H, J=5.1 Hz), 7.76-7.78 (m, 2H), 7.48 (d, 1H, J=5.5 Hz), 7.36 (t, 2H, J=7.5 Hz), 7.22 (d, 3H, J=7.5 Hz), 6.73-6.74 (m, 2H), 4.94-4.96 (m, 1H), 4.49 (dt, 1H, J=11.5, 6.0 Hz), 3.88-3.95 (m, 2H), 3.65 (t, 2H, J=14.6 Hz), 3.28-3.30 (m, 1H), 2.83 (d, 1H, J=8.0 Hz), 2.75 (t, 1H, J=8.5 Hz), 2.64 (q, 1H, J=12.4 Hz), 1.08 (d, 3H, J=6.5 Hz), 1.03 (d, 3H, J=7.1 Hz).

Pharmaceutical Composition

As a specific embodiment of this invention, 100 mg of N-[(3S,5S,6R)-6-Methyl-2-oxo-5-phenyl-1-(2,2,2-trifluoroethyl)piperidin-3-yl]-2'-oxo-1',2'-dihydro-3H-spiro[1-benzofuran-2,3'-pyrrolo[2,3-b]pyridine]-5-carboxamide is formulated with sufficient finely divided lactose to provide a total amount of 580 to 590 mg to fill a size 0, hard-gelatin capsule.

What is claimed is:

1. A compound of the Formula:

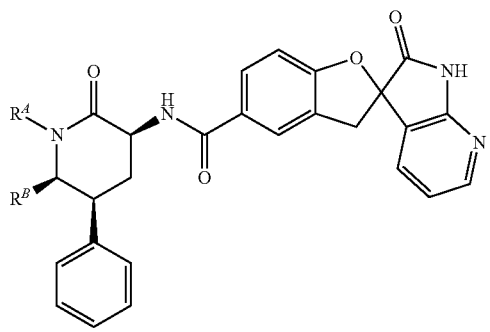

wherein, $R^A$ and $R^B$ are $C_{1-6}$-alkyl optionally substituted with halogen.

2. A pharmaceutical composition comprising a compound of claim 1, and a pharmaceutically acceptable carrier.

3. A compound of claim 1 which is: N-[(3S,5S,6R)-6-Methyl-2-oxo-5-phenyl-1-(2,2,2-trifluoroethyl)piperidin-3-yl]-2'-oxo-1',2'-dihydro-3H-spiro[1-benzofuran-2,3'-pyrrolo[2,3-b]pyridine]-5-carboxamide or a pharmaceutically acceptable salt thereof.

* * * * *